United States Patent
Xu et al.

(10) Patent No.: US 6,374,860 B2
(45) Date of Patent: Apr. 23, 2002

(54) INTEGRATED VALVE DESIGN FOR GAS CHROMATOGRAPH

(75) Inventors: Yang Xu, Houston; Teresa Lechner-Fish, Katy, both of TX (US)

(73) Assignee: Daniel Industries, Inc.

( * ) Notice: Subject to any disclaimer, the term of this patent is extended or adjusted under 35 U.S.C. 154(b) by 0 days.

(21) Appl. No.: 09/174,131

(22) Filed: Oct. 16, 1998

(51) Int. Cl.$^7$ ............... E03B 1/00; E03C 1/00; F16K 1/00; F17D 1/00

(52) U.S. Cl. ............... 137/884; 137/883; 137/885; 73/19.02

(58) Field of Search ............... 137/883, 884, 137/885; 73/19.02

(56) References Cited

U.S. PATENT DOCUMENTS

| | | | | |
|---|---|---|---|---|
| 3,057,376 A | * | 10/1962 | Agutter et al. | 137/594 |
| 3,312,238 A | * | 4/1967 | Voit, Jr. | 137/552.5 |
| 4,119,120 A | * | 10/1978 | Mehaffy et al. | 137/885 |
| 4,353,243 A | * | 10/1982 | Martin | 73/23.42 |
| 4,858,883 A | * | 8/1989 | Webster | 251/61.1 |
| 5,083,742 A | * | 1/1992 | Wylie et al. | 251/61.1 |
| 5,176,359 A | | 1/1993 | Leveson et al. | 251/61.1 |
| 5,325,889 A | | 7/1994 | Paul et al. | 137/594 |
| 5,361,802 A | * | 11/1994 | Kroll et al. | 137/552 |
| 5,544,276 A | | 8/1996 | Loux et al. | 392/480 |
| 5,601,115 A | | 2/1997 | Broerman | 137/595 |
| 5,653,259 A | | 8/1997 | Ramstad | 137/606 |

FOREIGN PATENT DOCUMENTS

WO    WO98/11431    3/1998

* cited by examiner

Primary Examiner—A. Michael Chambers
(74) Attorney, Agent, or Firm—Conley, Rose & Tayon, P.C.

(57) ABSTRACT

A gas chromatograph with multiple valves is disclosed. An embodiment of the multi-valve gas chromatograph includes multiple valves, multiple thermal conductivity detectors (TCD's), and a manifold. This allows separation and measurement of a gas sample in one compact integrated unit. The unit is particularly desirable because the solenoids associated with the valves are attached directly to the underneath of the manifold, thus eliminating the need for tubing between the solenoids and the valves.

Other features may also be present. For example, a leak free multi-valve block may include a first temperature zone heating the valves and detectors and a second temperature zone heating the columns. The leak free feature may be achieved by placement of tightening screws through the center of each valve. Carrier gas insertion areas may be provided in the multi-valve block to improve performance. Improved separation of the temperature zones leading to further gains in performance can be achieved by use of both a thermal insulator and an air gap. Further, the temperature sensors placed in the first temperature zone can be ideally located to minimize measurement error, resulting in yet further performance gains.

26 Claims, 24 Drawing Sheets

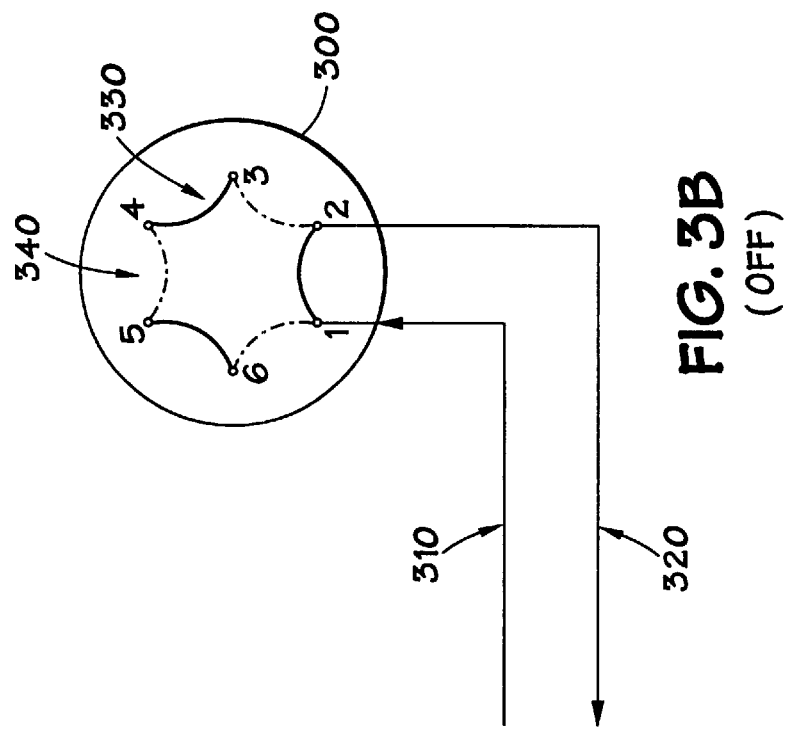
FIG. 3B (OFF)
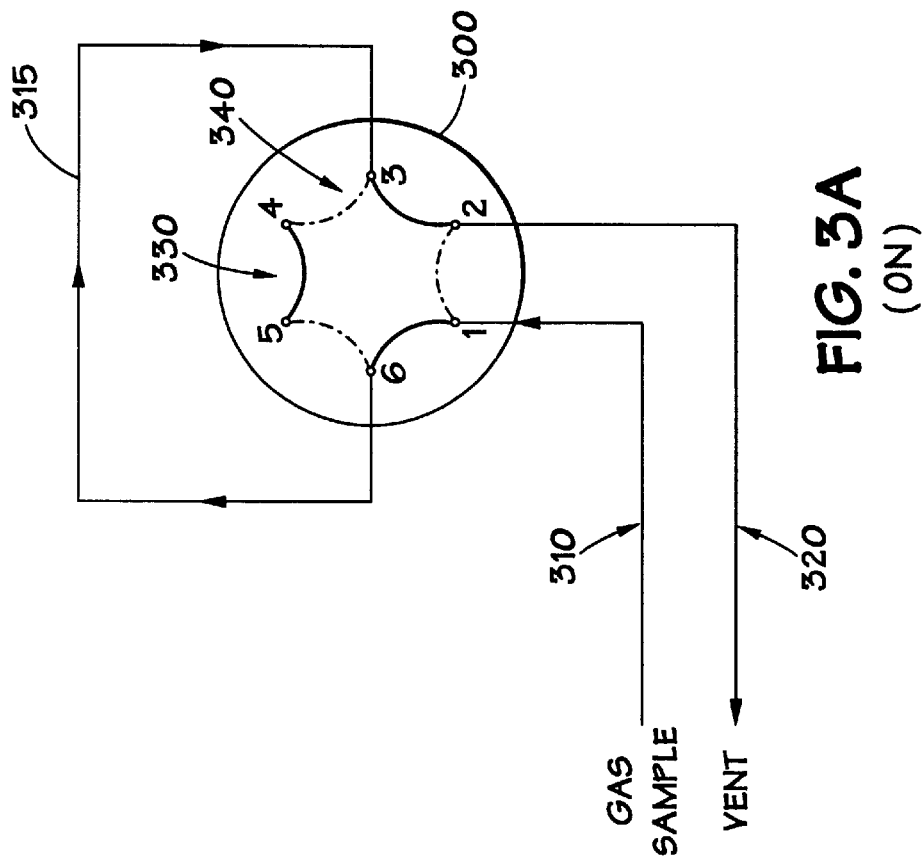
FIG. 3A (ON)

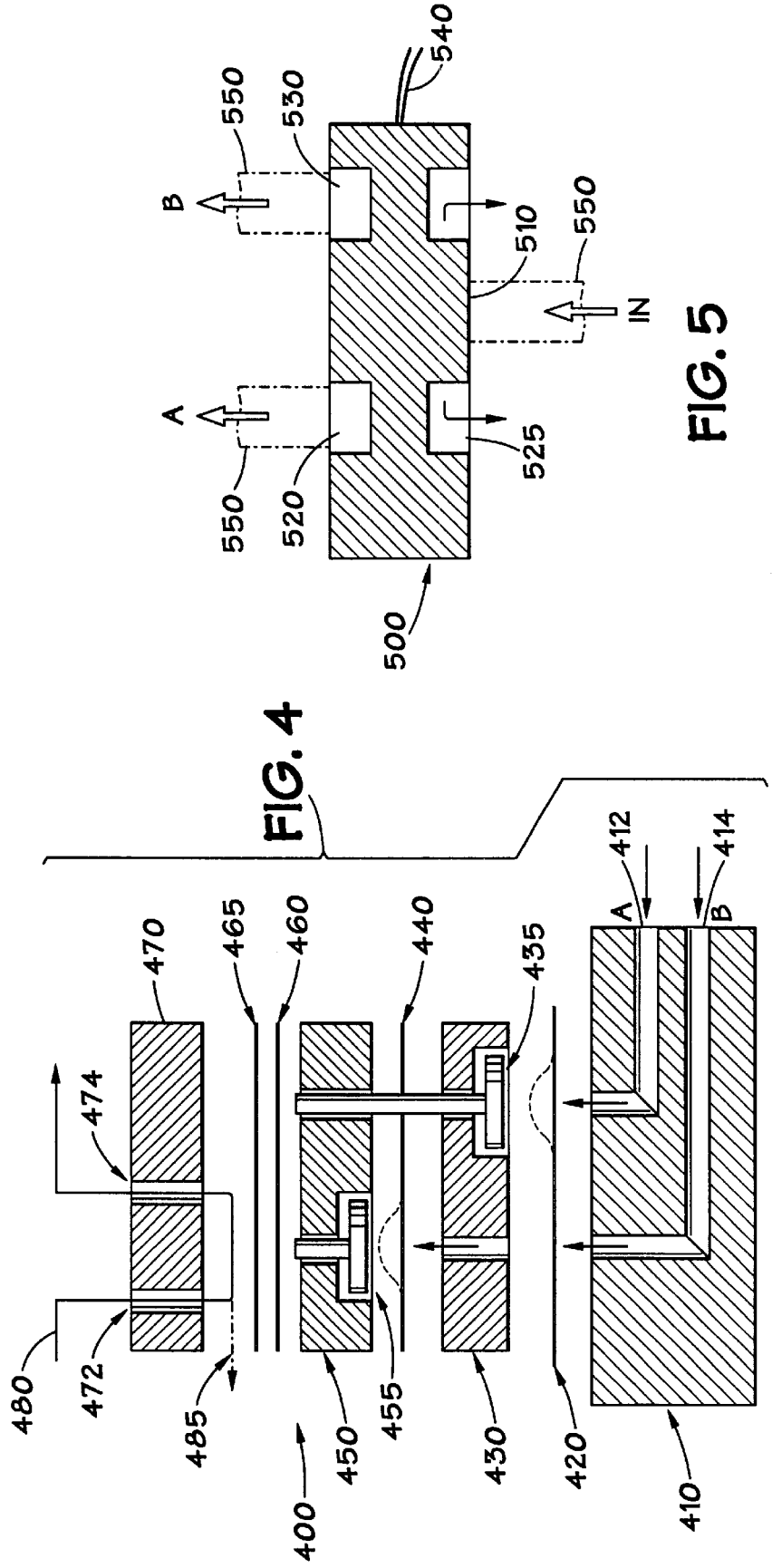

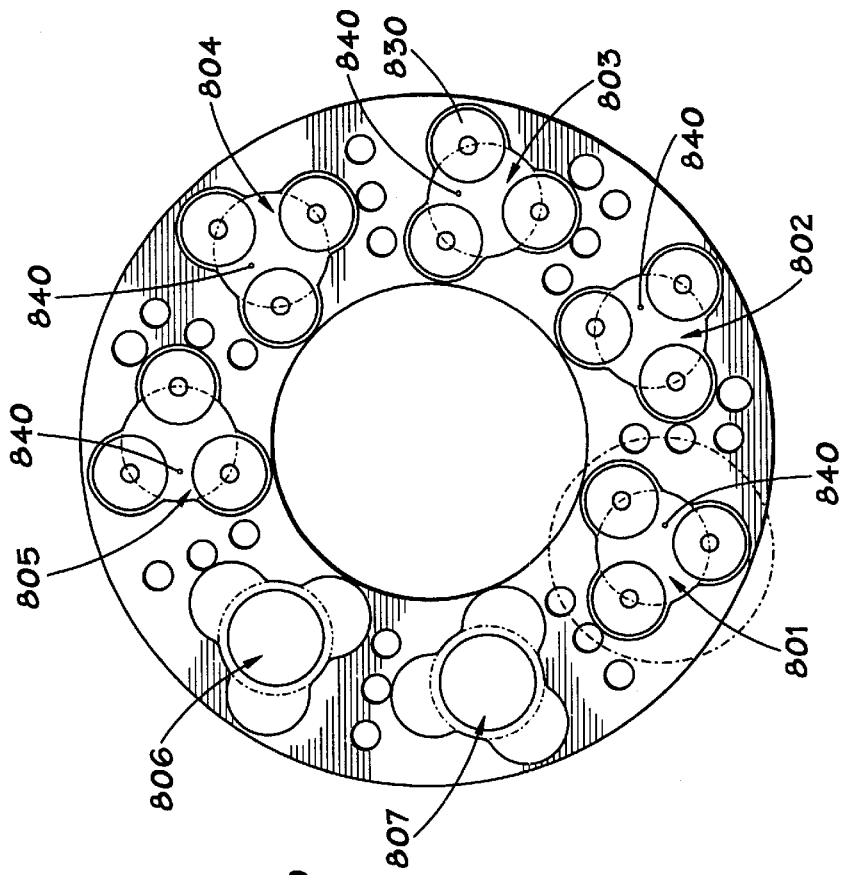
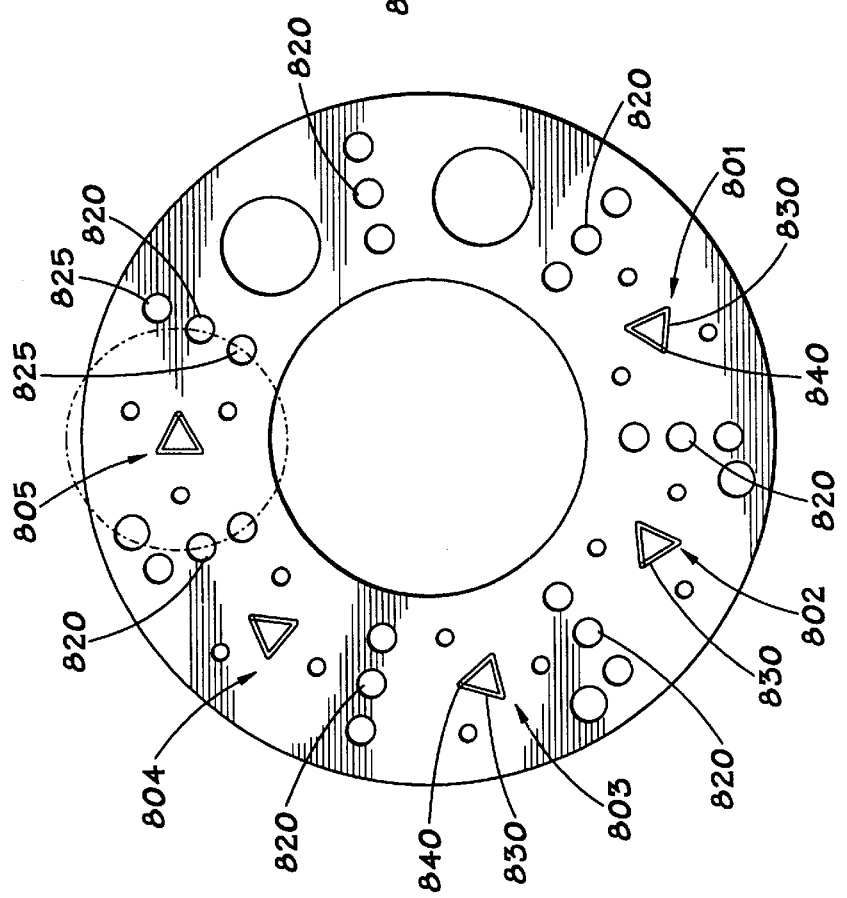

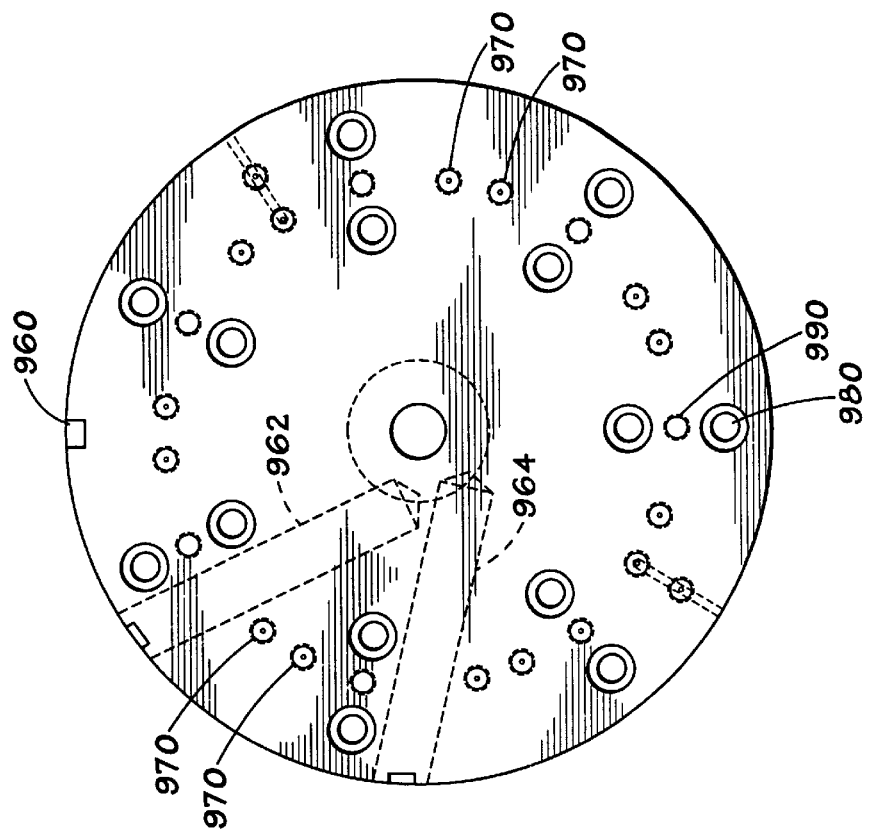
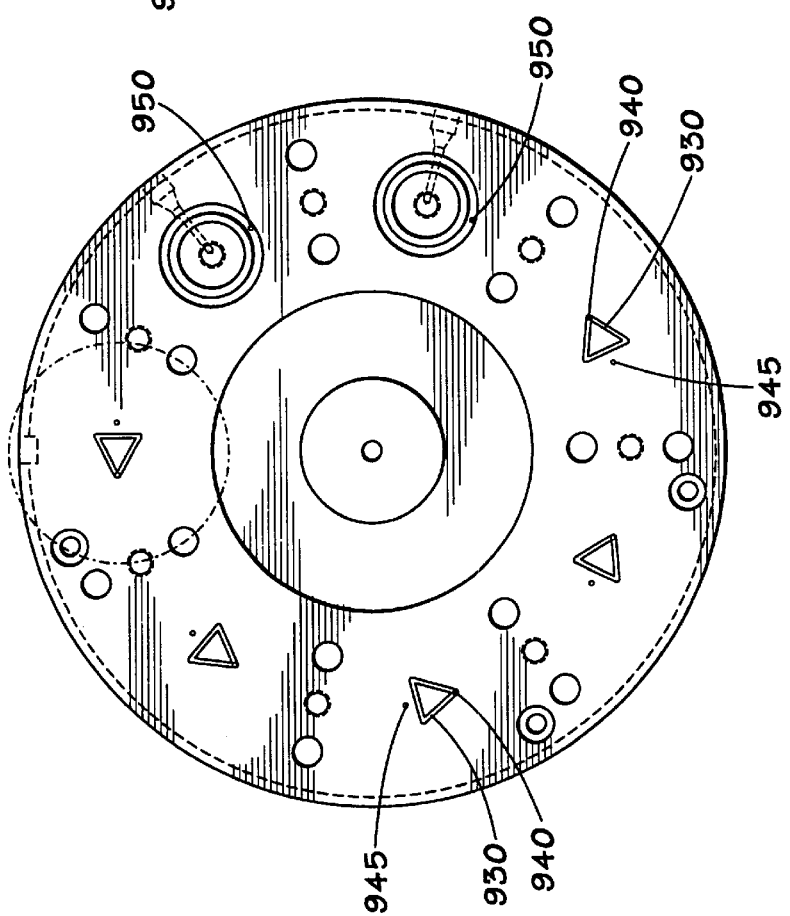

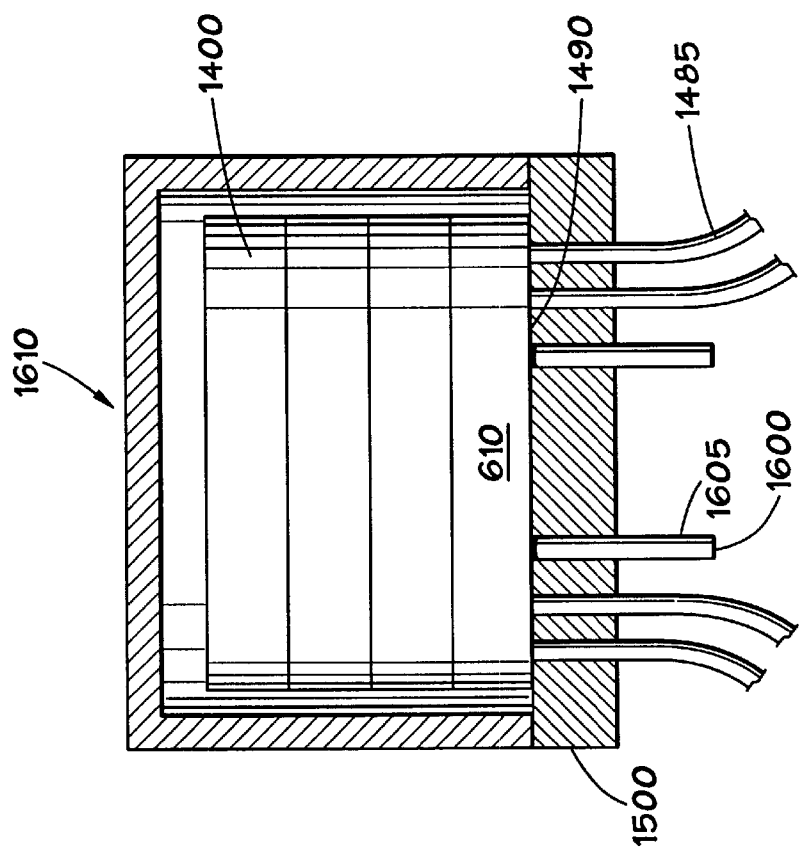
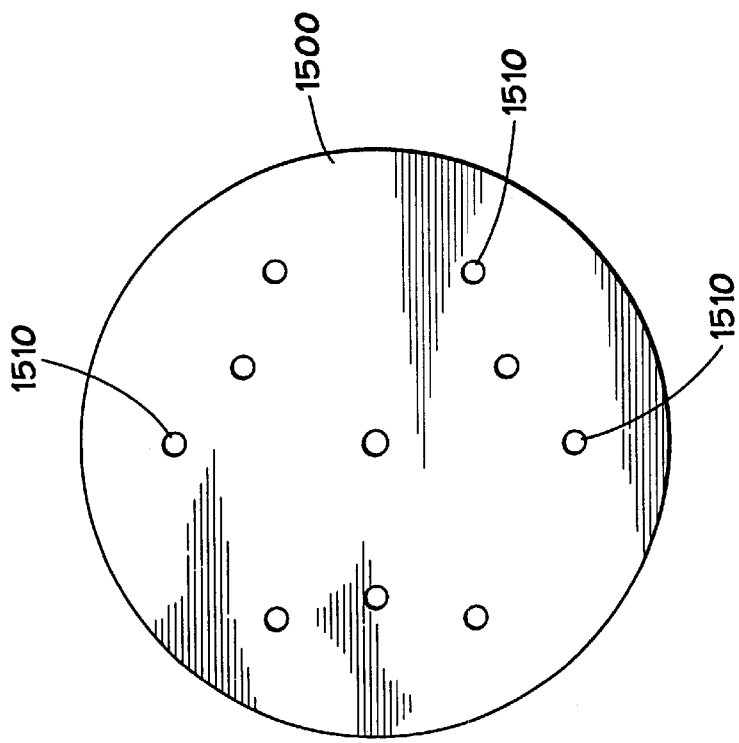

INTEGRATED VALVE DESIGN FOR GAS CHROMATOGRAPH

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

This invention relates to the field of gas chromatography. In particular, this invention relates to a new gas chromatograph. Even more particularly, this invention relates to a new gas chromatograph having multiple valves and detectors.

2. Description of the Related Art

The field of gas chromatography is concerned with analyzing gas samples flowing through a process pipeline. A sample is provided to a gas chromatograph, which then separates the sample into portions and uses a variety of detectors to analyze the concentration of particular components in the process stream.

Before now, a number of problems have existed with gas chromatographs. For example, fast and accurate measurements are desirable for any gas chromatograph. A gas stream flowing through the process pipeline may be composed of many different classes of components and ideally, each of these components would be analyzed. However, conventional gas chromatographs cannot respond to process changes as quickly as desired. Further, liquid contaminants in the process stream can introduce further complications to any analysis.

Another problem with previous gas chromatographs is a lack of flexibility in analysis of the gas stream. It would often be desirable to analyze different characteristics of the gas stream without switching to another gas chromatograph. However, previous gas chromatographs are restricted because of their limited number of valves and by their lack of flexibility. As such, a gas chromatograph is needed that can analyze complex process streams with greater accuracy and speed.

Other problems with gas chromatographs have also existed in the valve system contained in gas chromatographs. For example, these valves are not easy to service. Maintenance may be necessary because often the flows through a gas chromatograph are dirty, and this contamination can affect the performance of key components in the gas chromatograph. Substitution of clean components in the gas chromatograph can minimize the problem, but disassembling the gas chromatograph has in the past been a difficult and frustrating experience. Thus, a need for a new gas chromatograph exists.

As known by those of ordinary skill, the prior art also presents other problems that should be solved or minimized.

SUMMARY OF THE INVENTION

A disclosed embodiment includes a multi-valve assembly. This multi-valve assembly includes a plurality of plates and diaphragms attached together to form a plurality of valves. One of these plates is a manifold that includes a common line passage and a plurality of actuation passages, at least one of the activation passages being connected to the common line passage, there being at least as many actuation passages as there are valves. Alternately, this embodiment may be seen as a multi-valve device including at least two valves integrated into a first region that includes a first region, a gas stream property detector such as a TCD, and a first temperature sensor. A second region integrates a second heater and a second temperature sensor, with the first region's temperature sensor and gas stream property detector lying on the same radial curve with respect to a point lying in the second region.

The invention comprises a combination of features and advantages which enable it to overcome various problems of prior devices. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawings, wherein:

FIG. 3A is a schematic diagram of a valve in an ON configuration.

FIG. 3B is a schematic diagram of a valve in an OFF configuration.

FIG. 4 is an illustrative cut-away view of a valve.

FIG. 5 is an illustrative cut-away view of a solinoid.

FIG. 8A is a top view of a lower piston plate for the multi-valve block of FIG. 6.

FIG. 8B is a bottom view of a lower piston plate for the multi-valve block of FIG. 6.

FIG. 9A is a top view of a base plate for the multi-valve block of FIG. 6.

FIG. 9B is a bottom view of a base plate for the multi-valve block of FIG. 6.

FIG. 15 is a top view of the bottom piece of insulation for a multi-valve assembly oven.

FIG. 16 is a cross-section view of an embodiment of the multi-valve assembly.

DETAILED DESCRIPTION OF THE PREFERRED EMBODIMENT

Figure 1:
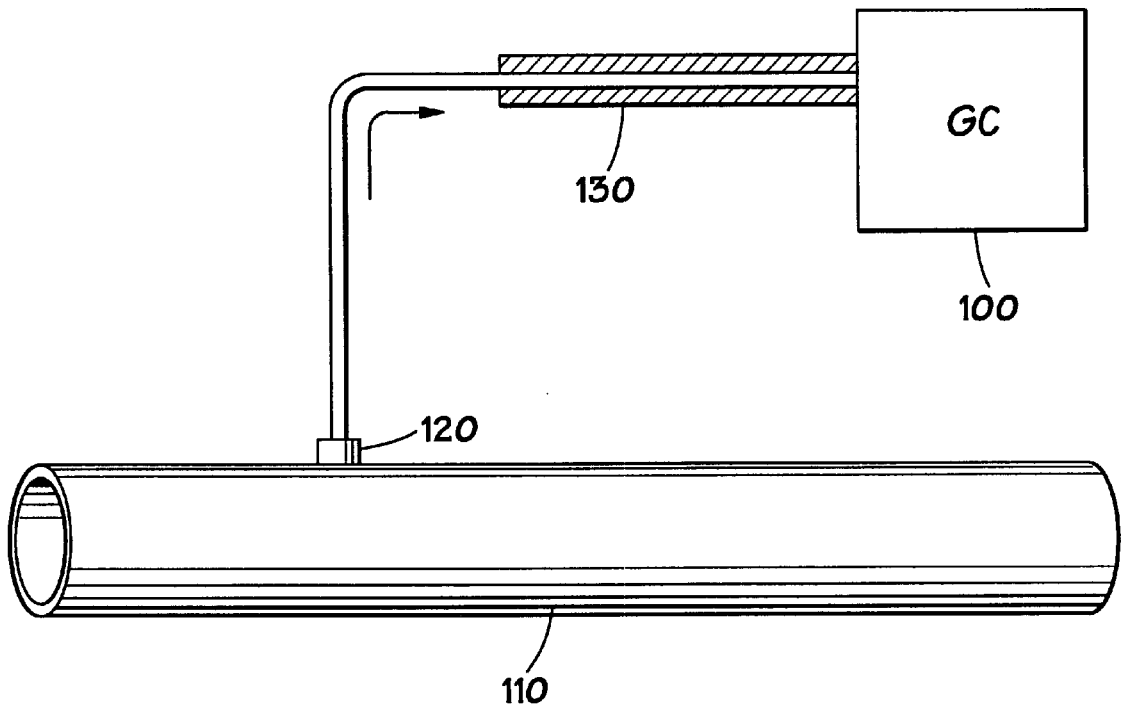
FIG. 1 is a simplified diagram of a gas chromatograph system.

FIG. 1 shows a gas chromatograph system generally built in accordance with the teachings herein. Gas flows through a process pipeline 110, a sample of which is taken by a sample probe 120 prior to being introduced to gas chromatograph (GC) 100. The gas sample may be filtered and heat traced generally along tubing 130 before flowing into gas chromatograph 100. This heating may be required for gases that may condense into a part gas, part liquid flow at cooler temperatures. After being analyzed by the gas chromatograph, the gas sample is either returned into the process pipeline 110, or vented to the atmosphere.

Figure 2:
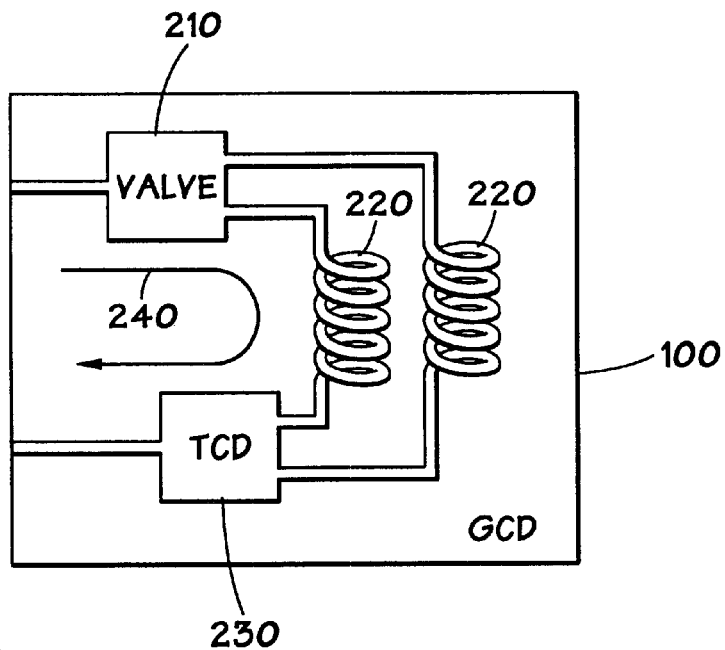
FIG. 2 is a simplified schematic of a gas chromatograph.

Referring to FIG. 2, gas chromatograph 100 includes valve assembly 210 connected to multiple columns 220 and detectors 230, in this case, thermal conductivity detectors (TCD). A gas sample generally follows path 240 through valve assembly 210, columns 220 and TCDs 230. The valve assembly allows the selection of columns 220 which contain a liquid phase, or porous polymer, or other material that acts to separate the gas sample into multiple portions, each portion being sequentially released to the TCDs 230. For example, a gas sample may contain various molecular weight hydrocarbon components. Column 220 could separate the gas sample so that lower molecular weight hydrocarbon components would elute from the column first, followed by a higher molecular weight component, etc.

Referring to FIGS. 3A and 3B, the operation of a valve is shown. Valve 300 includes a plurality of valve ports, labeled 1–6. It will be appreciated that more or fewer number of ports may also be used. Incoming line 310 provides a gas sample to valve 300. Exhaust line 320 expels the gas sample from the valve 300. Solid lines 330 show open passages between ports, whereas dotted lines 340 indicate blocked passages between the ports.

A solenoid (not shown) places valve 300 into either an ON position, as shown in FIG. 3A, or an OFF position, as shown in FIG. 3B. When a valve is in the ON position, gas flows from incoming line 310, through port 1 to port 6, through line 315 and finally through port 3 to port 2 and out exhaust line 320. When the valve is in the OFF position, gas flows from incoming line 310, through port 1 to port 2 and out through exhaust line 320.

Figure 3C:
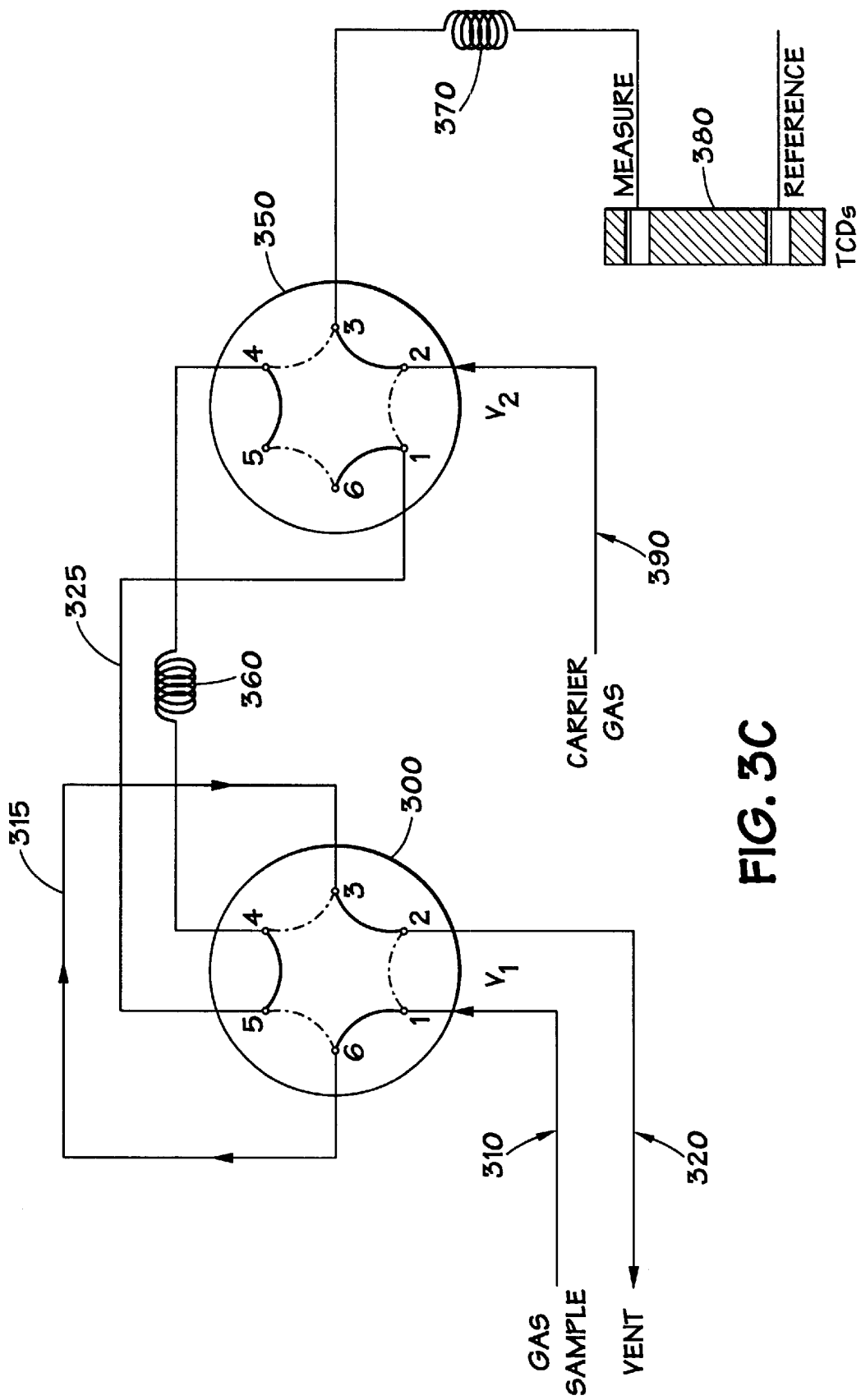
FIG. 3C is a schematic diagram of a multiple valve system for analyzing a sample.

FIGS. 3C and 3D illustrate how a pair of valves may operate either alone or in combination with additional valves (not shown). A first valve 300 includes an array of 6 valve ports. A second valve 350 also includes an array of 6 valve ports. Associated tubing 310, 315, 320, 325 and 390, and columns 360 and 370 are also shown as well as dual TCD 380.

Incoming line 310 is attached to a sample transport line (not shown). When first valve 300 in an OFF position, gas sample flows from incoming line 310 to port 1 to port 2 of the valve 300 and out exhaust line 320. When valve 300 is in an ON position, however, gas sample flows from port 1 to port 6 and then through sample loop 315. That gas then flows from port 3 to port 2 of valve 300 and is expelled out exhaust line 320. At this time, the sample loop 315 is filled with a gas sample. This means that, if valve 300 is turned OFF at this time, a gas sample is trapped within the sample loop 315.

Turning now to valve 350, when it is in an OFF configuration, carrier gas flows from carrier gas input line 390 through port 2 of valve 350, to port 1 and then through carrier tubing 325. At this time, valve 300 is also in an OFF configuration, so that the carrier gas in tubing 325 is forced through port 5 to port 6 and through gas sample tubing 315. Consequently, this action forces the gas sample down column 360 via ports 3 and 4. The gas sample can then additionally be forced through column 370 and into the dual TCD 380 via ports 4 and 3. Many other port combinations also exist and are within the skill of one in the art. Thus, the valves may be connected in series to form "channels."

Each channel feeds into a corresponding TCD pair (a measurement TCD and a reference TCD). Use of more than one TCD pair results in a simultaneous analysis by the TCD's of the sample flowing through their corresponding attached columns. This parallel analysis results in a increased analysis speed as compared to serial analysis. Further, because technology currently limits the channels and the detector pairs to a one-to-one correspondence, the number of channels in use at any particular time is limited both by the number of valves and by the number of detectors. Of course, the greater the number of valves, the greater the number of potential channels, and the more potential for more parallel processing and a faster overall system. But even if the number of detectors limits the number of channels being used at any one time, a greater number of valves results in a greater number of channels from which to choose for each TCD. For example, a multi-valve system may have sufficient valves to operate eight channels. Even if only two detector pairs exist, such that only two channels can be in use at any one time, the detector pairs can be designed to select which channel among those eight channels it is connected to. This dramatically increases the flexibility of the presently disclosed gas chromatograph system.

Referring to FIG. 4, a cross-section of a partial valve assembly is shown. Valve 400 includes a base plate 410 with activation ports 412 and 414, a lower actuator diaphragm 420, a lower piston plate 430 with associated long piston 435, upper actuator diaphragm 440, upper piston plate 450 with associated short piston 455, cushion diaphragm 460, sealing diaphragm 465, and primary plate 470 with valve ports 472 and 474 therein. These valve ports suitably could be ports 1 and 6 as shown in FIG. 3.

Referring back to FIG. 4, gas sample 480 enters valve port 472. This gas sample 480 travels out valve port 474 when long piston 435 is in an elevated (closed) position and short piston 455 is not. Long piston 435 is elevated by gas pressure applied to activation port A 412. This pressure deforms lower actuator diaphragm 420 and forces long piston 435 in an upward direction in lower piston plate 430. Upper end of long piston 435 then abuts against primary plate 470. Similarly, short piston 455 is actuated by gas pressure from activation port B 414, and forces gas sample 480 to path 485.

Whether a valve is in an ON or OFF position depends upon a solenoid that applied gas pressure alternately to either activation port A or activation port B. FIG. 5 generally illustrates the operation of a solenoid. Solenoid 500 includes a common line port 510, exit port 520 corresponding to activation port A, exit port 530 corresponding to activation port B, release port 525 for exit port A or exit port B, and control leads 540. Tubing 550 connects to each of common line port 510, and exit ports 520 and 530. Exit ports A and B connect to activation ports A and B in FIG. 4, respectively. Common line port 510 connects to a gas under pressure. Gas pressure applied to either of activation port A or activation port B controls whether the corresponding valve is in an ON or OFF position. Electrical control signals from leads 540 control whether common line 510 is connected to exit port A or exit port B, and thus whether gas pressure is applied to activation port A or activation port B. Some variation to the particulars of this design is possible while still staying within the teachings of the invention.

Figure 6:
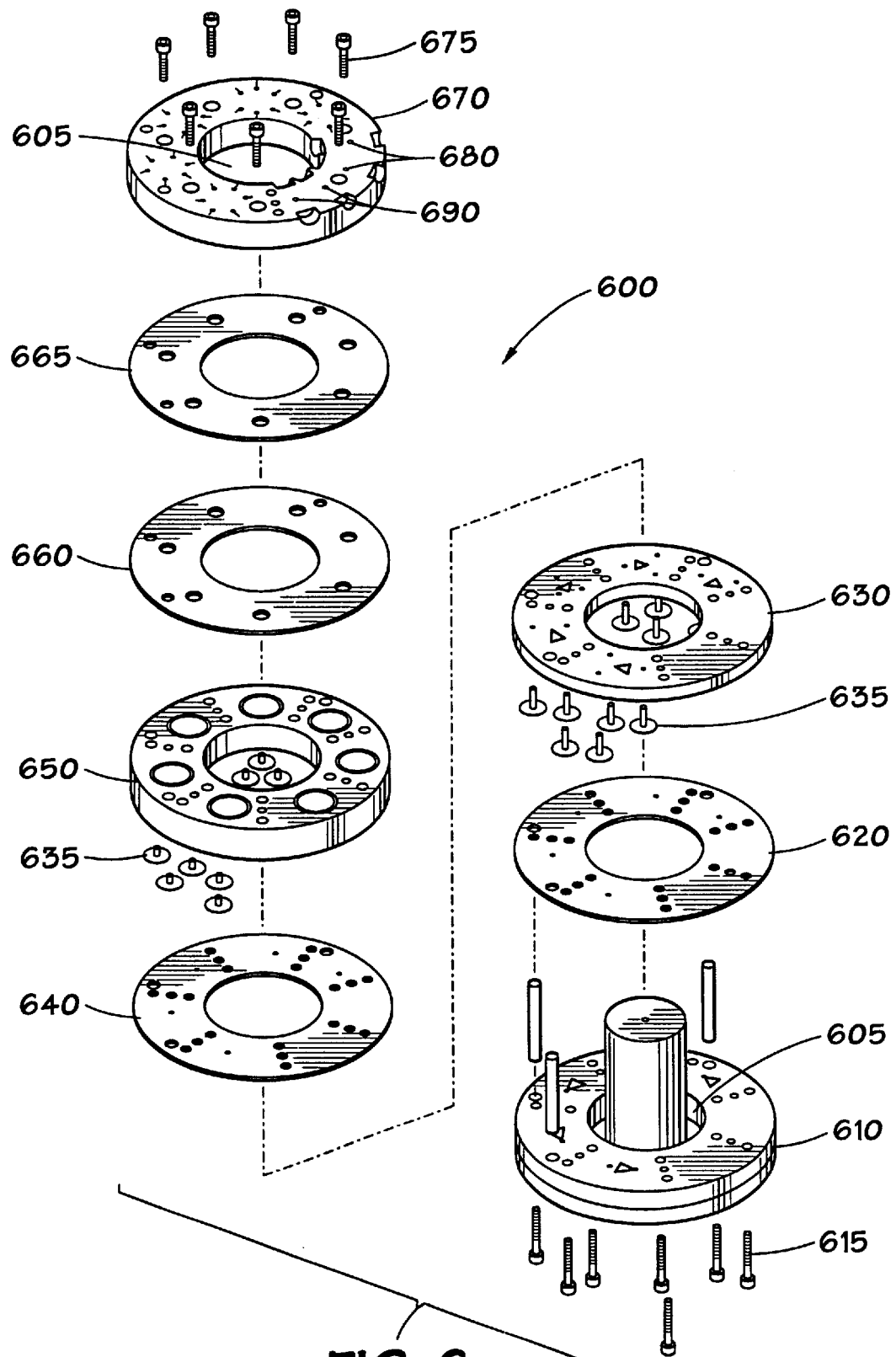
FIG. 6 is an exploded isometric view of an embodiment of a multi-valve block.

FIG. 6 shows an exploded view of an embodiment of the multi-valve block 600 including an open area 605, base plate 610 with associated dowel pins to align components, a lower activator diaphragm 620, a lower piston plate 630 with associated long pistons 635, an upper activator diaphragm 640, an upper piston plate 650 with associated short pistons 655, a cushion diaphragm 660, a sealing diaphragm 665, and a primary plate 670. Each piston includes a lower base portion with a pole extending therefrom. Hole sets 680 and 690 are suitable for two pairs of TCD'S. First set of screws 615 for insertion through base plate 610, lower piston plate, and upper piston plate are shown as well as a second set of screws 675 for insertion through primary plate 670, upper piston plate 650, and lower piston plate 630. In addition, because there are five valves, five solenoids (not shown) are also present, each controlling a different valve.

As can be seen, the multi-valve device 600 includes 5 valves, with each valve having six ports. By integrating multiple valves into a single multi-valve block, a compact device is achieved that can separate a gas sample into a large number of columns as discussed above. This facilitates faster and more precise analysis of the gases contained in the gas sample. Manufacturing costs can also be reduced. The teachings herein can be used to integrate more or fewer than 5 valves into a single unit, and more or fewer valve ports per valve. For example, if a greater number of valves is desired, up to 7 valves can easily be located in the embodiment shown in FIG. 6.

One manner in which the embodiment of FIG. 6 makes faster and more precise analysis of the gas sample is reduction of what is known as "dead volume." Increased dead volume results when the components of a gas chromatograph are widely spaced and undue mixing of the fluid occurs. This mixing of the gas or fluid sample results in a "band broadening." Band broadening is undesirable because the area of a band of an analysis corresponds to concentration and these bands should not overlap. Consequently, a series of broad bands results in a much slower analysis than is possible with a series of short, compact bands. Therefore, an integrated, compact design is particularly desirable from a performance perspective. Further, the illustrated geometry provides sufficient area for a first and second set of TCD's. While these TCD's may be located outside the multi-valve block if desired (e.g. to integrate a greater number of valves into the multi-valve block), the inclusion of the TCD's in the multi-valve block helps further miniaturize the device and make it more compact.

Figure 7B:
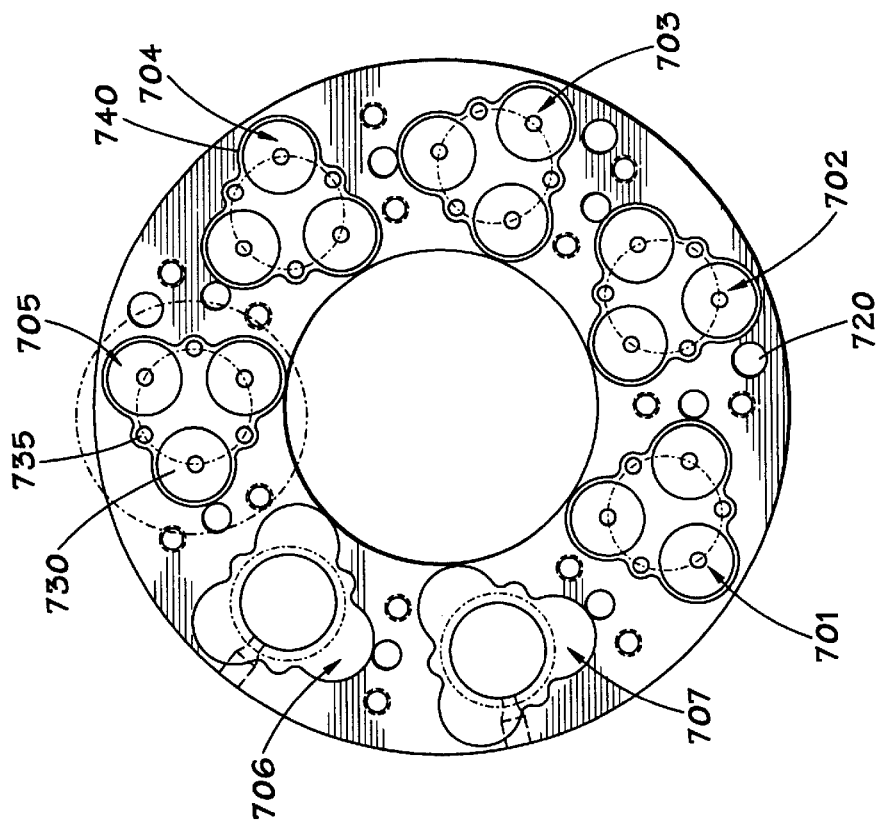
FIG. 7B is a bottom view of an upper piston plate for the multi-valve block of FIG. 6.
Figure 7A:
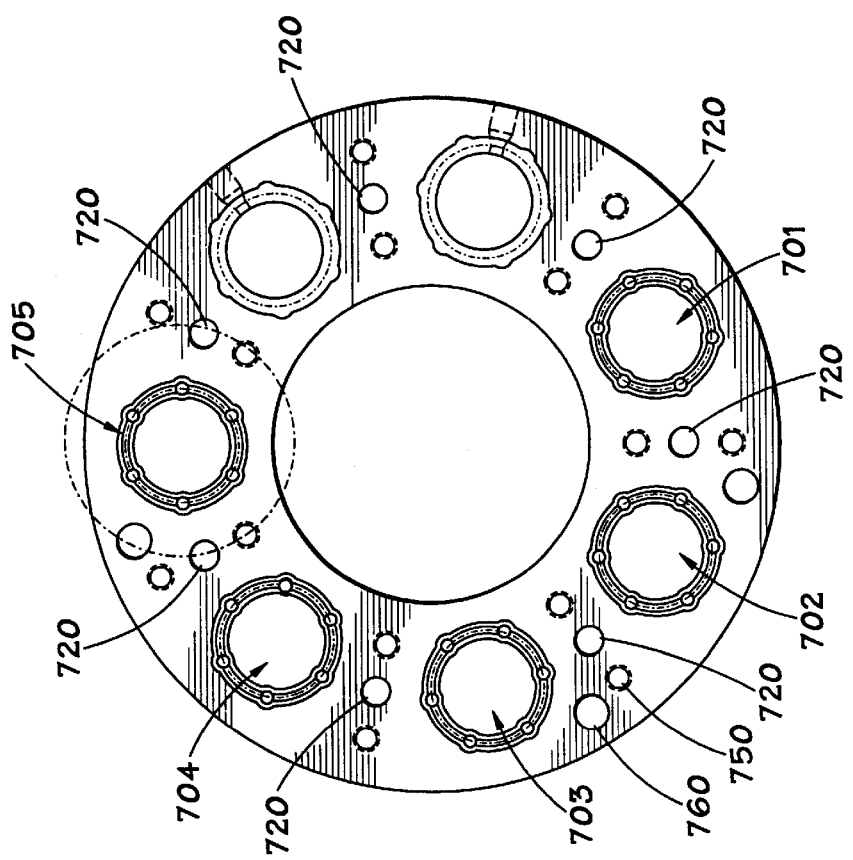
FIG. 7A is a top view of an upper piston plate for the multi-valve block of FIG. 6.

FIGS. 7A and 7B show top and bottom views respectively of the upper piston plate of FIG. 6. Referring to the top view of FIG. 7A, locations 701–705 for 5 valves are shown. Screw holes, generally at 720, are also shown for accepting screws to tighten together the primary plate with other plates. Holes 750 are for screws from the bottom to tighten the plates together, while holes 760 are fore dowel pins to position the valves. Turning to the bottom view of the upper piston plate shown in FIG. 7B, locations 701–707 are similarly shown. Each valve includes sufficient room 730, 735 for 3 piston bases and 3 piston poles. Raised edges 740 around the perimeter of each valve location are also shown. The raised surfaces defined by the raised edges exist on both sides of the upper and lower piston plates. A raised edge of 0.032 inches could be used, for example. These raised edges 740 reduce the surface area upon which the screws 615 and 675 provide force and thereby reduce the chance of leakage.

Referring back to FIG. 6, it can be seen that two sets of screws are shown corresponding to holes 720 and 750. These two sets of screws that protrude through holes 720 and 750 simplify maintenance of the invention. A bottom set of screws 615 extends through the base plate 610, lower piston plate 630, and upper piston plate 650. Screws 615 attach these plates together. A top set of screws 675 extends through the primary plate and the upper piston plate to hold those plates together. This dual screw set approach simplifies maintenance because the loosening and removal of screws 675 allows access and replacement of the sealing diaphragm 665 and cushion diaphragm 660 without disassembly of a greater number of plates than necessary. It is the sealing diaphragm that becomes most contaminated by the dirty gas that flows through the multi-valve. A relatively low torque of about 10 ft/lbs. has been found acceptable for these screw sets while making the removal of these screws as easy as possible. The multi-valve configuration also simplifies maintenance because, by virtue of multiple valves in an integrated unit, replacement of only one diaphragm is necessary rather than the multiple diaphragms that would otherwise be necessary for multiple valves.

FIGS. 8A and 8B show the lower piston plate of FIG. 6. FIGS. 8A and 8B are the upper and lower views respectively of the lower piston plate. Referring to FIG. 8A, once again, locations 801–805 are provided for the five valves, in addition to an area for two sets of TCDs. Holes 820 and holes 825 accept tightening screws. Also shown are five triangular grooves 830 and accompanying holes 840 within each groove. Gas from the solenoids travels through the actuation holes 840 to the grooves 830. These grooves 830 provide a path for the actuation gas that elevates the short pistons. Because the valves of the illustrated embodiment have six ports, and thus three short pistons per valve, a triangular shape is convenient (but not necessary) to actuate all three short pistons simultaneously. Turning now to the bottom view of FIG. 8B, locations 801–807 are shown. Also generally shown at 840 are holes connected to an actuator port through which gas exerts pressure. These holes 840 correspond to the grooves 830 of FIG. 8A. As can be seen, space 830 is provided for the base of long pistons 635.

FIGS. 9A and 9B show the top and bottom views respectively of the base plate. Referring to FIG. 9A, similar to FIG. 8A, a plurality of grooves 930 are shown, with each groove encompassing a hole 940 for actuator gas. In addition, actuator holes 945 traveling up to the lower piston plate are additionally shown. FIG. 9B illustrates the bottom view of the base plate. Illustrated are slot 960 and holes 970, 980, and 990. Slot 960 is present because it simplifies the removal of diaphragms upon disassembly. In particular, after a valve has been assembled, the diaphragms tend to stick to a contact surface, and the slots provide an area where the diaphragms can be easily grabbed onto. Hole 970 is a port A and B common line that connects to port A and B on solenoids via tubing. Holes 980 and 990 are screw holes. FIG. 9B also shows cross-drill lines 962 and 964 representing drilled areas for insertion of carrier and sample gas tubing. Holes at the entrance to each insertion area are also shown. The carrier and sample gas are quickly and reliably preheated in the insertion areas defined by cross-drill lines 962 and 964 from the warmth in the multi-valve block.

Figure 10B:
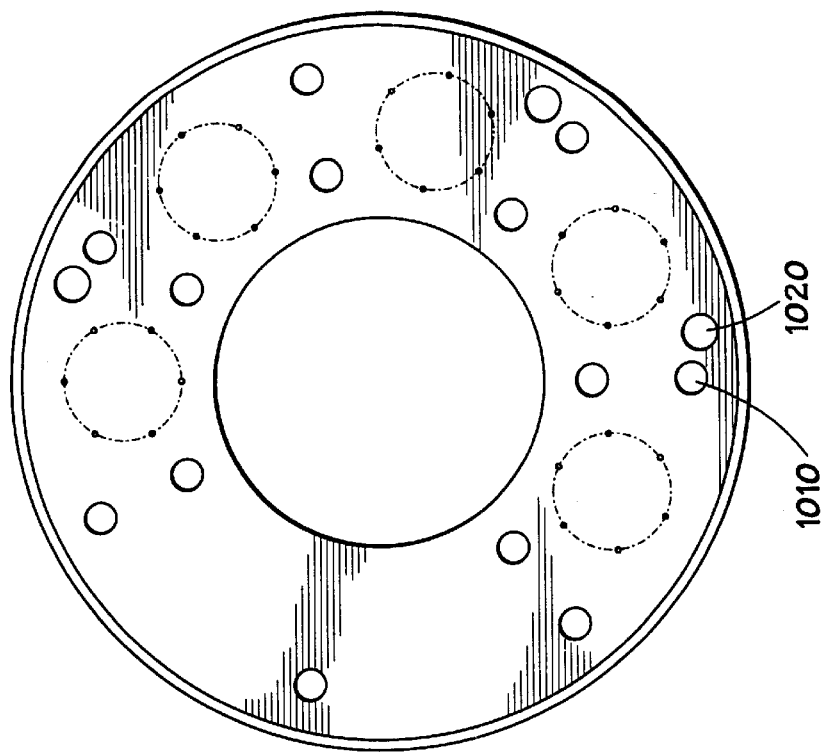
FIG. 10B is a bottom view of a primary plate for the multi-valve block of FIG. 6.
Figure 10A:
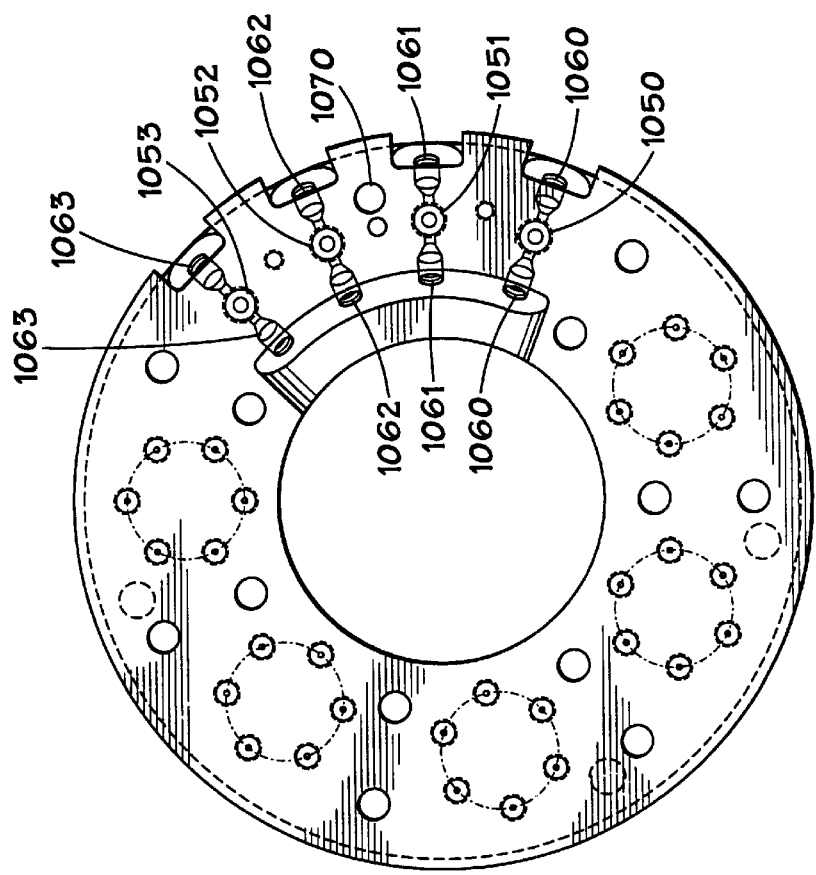
FIG. 10A is a top view of a primary plate for the multi-valve block of FIG. 6.

FIGS. 10A and 10B show the upper and lower view of a primary plate of FIG. 6. Referring now to FIG. 10A shown are TCD holes 1050–1053 and associated tubing holes 1060–1063. Also shown is a hole 1070 suitable for a RTD heat sensor. FIG. 10B shows a bottom view of the primary plate. Included are holes 1010 to accept screws and 1020 to accept dowel pins.

Figure 12:
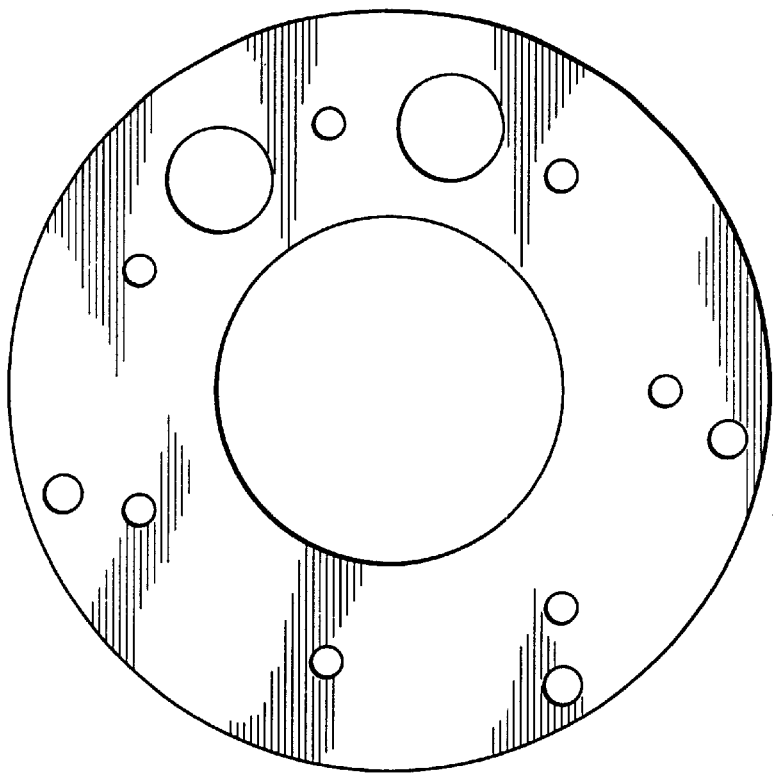
FIG. 12 is a cushion diaphragm for the multi-valve block of FIG. 6.
Figure 11:
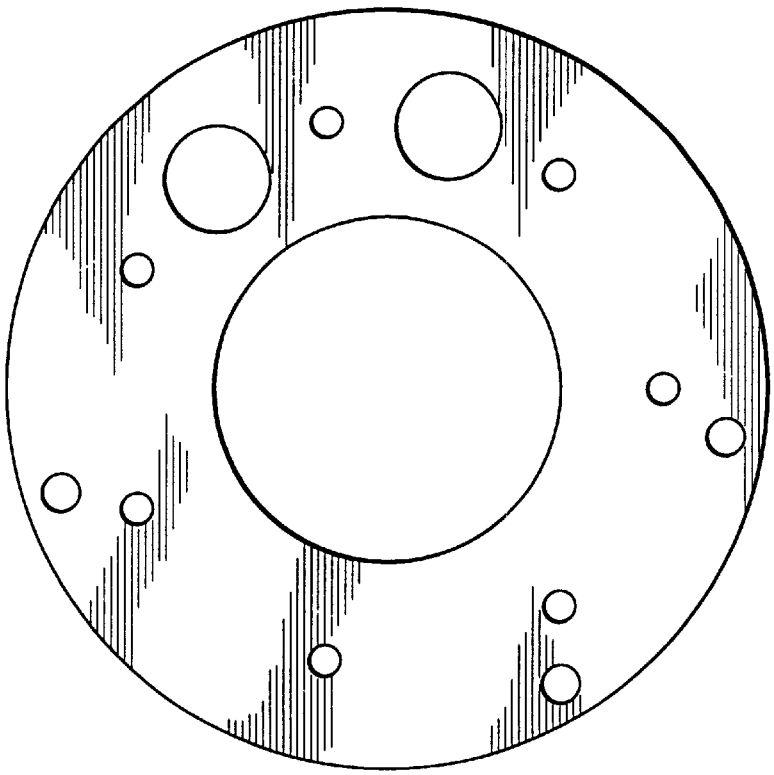
FIG. 11 is a sealing diaphragm for the multi-valve block of FIG. 6.
Figure 13B:
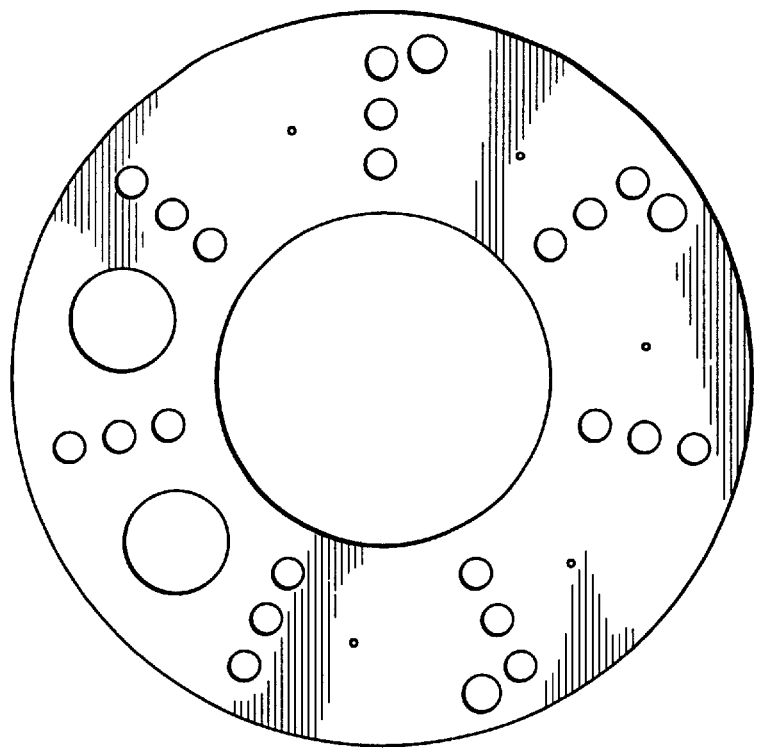
FIG. 13B is a lower actuator diaphragm for the multi-valve block of FIG. 6.
Figure 13A:
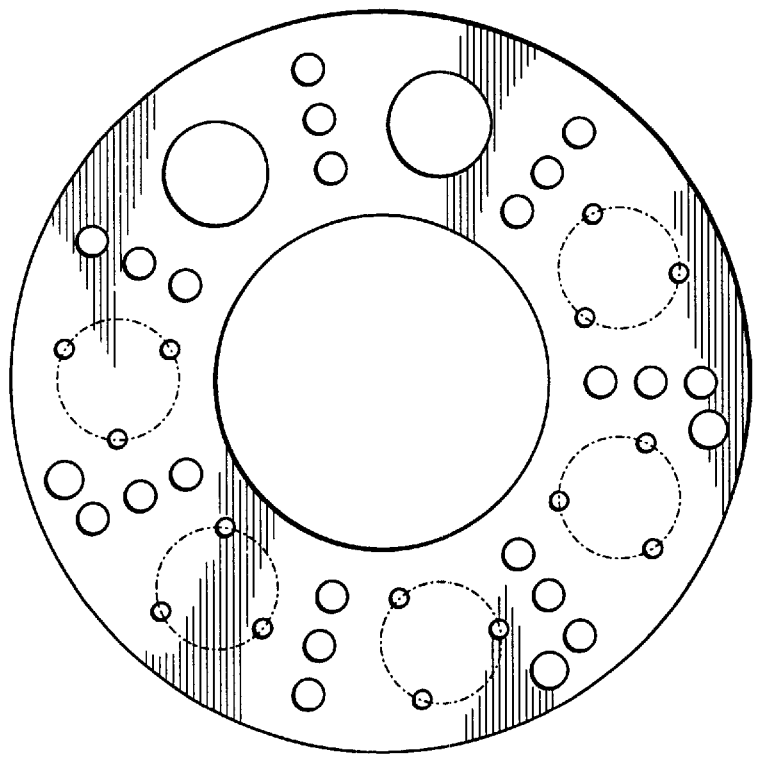
FIG. 13A is an upper actuator diaphragm for the multi-valve block of FIG. 6.

FIGS. 11–13 illustrate the diaphragms of FIG. 6. FIG. 11 shows the sealing diaphragm of FIG. 6. The sealing diaphragm is preferably made from 2 mil thick Kapton™ made by DuPont with a 0.5 mil teflon coating on each side. FIG. 12 shows the cushion diaphragm of FIG. 6. The cushion diaphragm is preferably about 0.002" thick and is made from Nomax paper by DuPont. FIGS. 13A and 13B illustrate upper and lower actuator diaphragms. Both actuator diaphragms are preferably made from 3 mm thick Kapton™ made by DuPont.

Figure 14:
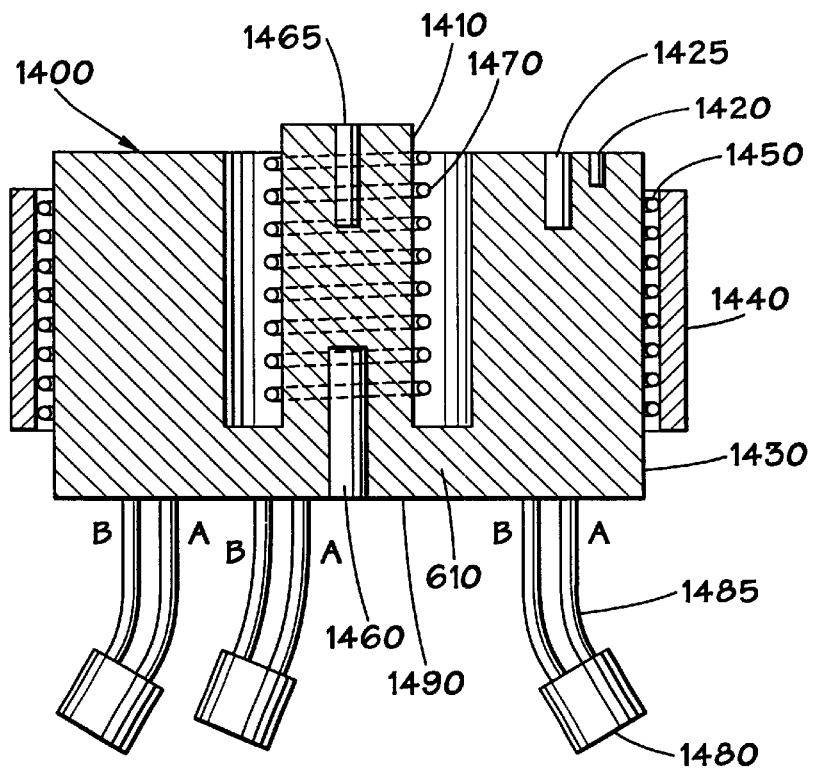
FIG. 14 is a cut-away view of a multi-valve assembly during operation.

FIG. 14 illustrates a multi-valve block 1400 including a spool 1410 with areas for a first RTD (Resistance Thermal Detector) 1420 and two TCD pairs 1425, an exterior surface 1430 to the multi-valve block 1400, a band heater 1440 outside of the exterior surface 1430, carrier gas preheat tubing 1450 located between the exterior surface 1430 and the band heater 1450, and a base plate 610 as part of the multi-valve block. Spool 1410 contains one or more cartridge heaters 1460 and a second RTD 1465. Referring back to FIG. 6, a hole or open area 605 is present in the middle of the multi-valve block. The open area 605 accommodates spool 1410 that protrudes from the base plate 610. Columns 1470 wraps around the spool 1410. Also shown are solinoids 1480 connected via tubing 1485 to the base plate at its lower end 1490. Band heater 1440 is an AC band heater of approximately 200 Watts power.

During operation, a gas sample flows through tubing or conduits 315 (not shown in FIG. 14) in the multi-valve block prior to flowing through the piping of the columns 1470. In contrast, the carrier gas flows through the carrier gas preheat tubing 1450 prior to flowing through columns 1470. The carrier gas preheat tubing may be located at different positions to heat the carrier gas to a predetermined temperature. The carrier gas preheat tubing may be just inside the band heater as shown in FIG. 14, or it may preferably occupy insertion areas in the multi-valve block, as explained in reference to FIG. 9. Thus, prior to being warmed by the spool, both the carrier gas and the gas sample are heated to approximately the temperature of the multi-valve block.

Thus, this arrangement provides for two heating zones. The area proximate to the spool 1410 defines a second heating zone. A first heating zone is defined by the temperature of the remainder of the multi-valve block. The first RTD located in the multi-valve block at 1420 measures the temperature of the first heating zone. The second RTD located at 1465 within the spool 1410 measures the temperature of the second heating zone. Two separate heating zones are important because the gas flowing through the columns 1470 should ideally be about 3–5° C. higher than the temperature at each TCD (the temperature of the first heating zone). In addition, the TCD's in the first heating zone should be kept to within about 0.1° C. of a predetermined temperature for accurate analysis. The temperature variation in the second heating zone should also be maintained within about a 0.1° C. tolerance. More heating zones may be added when desired to allow the analysis of the complex samples.

In order to stabilize the temperatures in heating zones, an "oven" is created from a thermal insulation material. This oven is essentially a cylindrical sleeve that surrounds the rest of the multi-valve device and keeps its temperature stable, except for the solinoids, which must be kept away from the heat inside the oven. Referring to FIG. 15, an illustrative bottom 1500 of this insulation cylinder or sleeve is shown. As can be seen, it contains a number of holes 1510, through which extend the tubing for the solenoids and the legs of the base stand.

FIG. 16 illustrates the insulation 1610 for the "oven" including the bottom 1500 of the insulation cylinder. As part of them multi-valve block 1400, base plate 610 is adjacent to the bottom of the insulation cylinder 1500. Legs 1600 to create stand-off are made from Teflon™ 1605. Also shown is tubing 1485 that extends through the bottom piece 1500 to the lower surface 1490 of the multi-valve block 1400.

Figure 17:
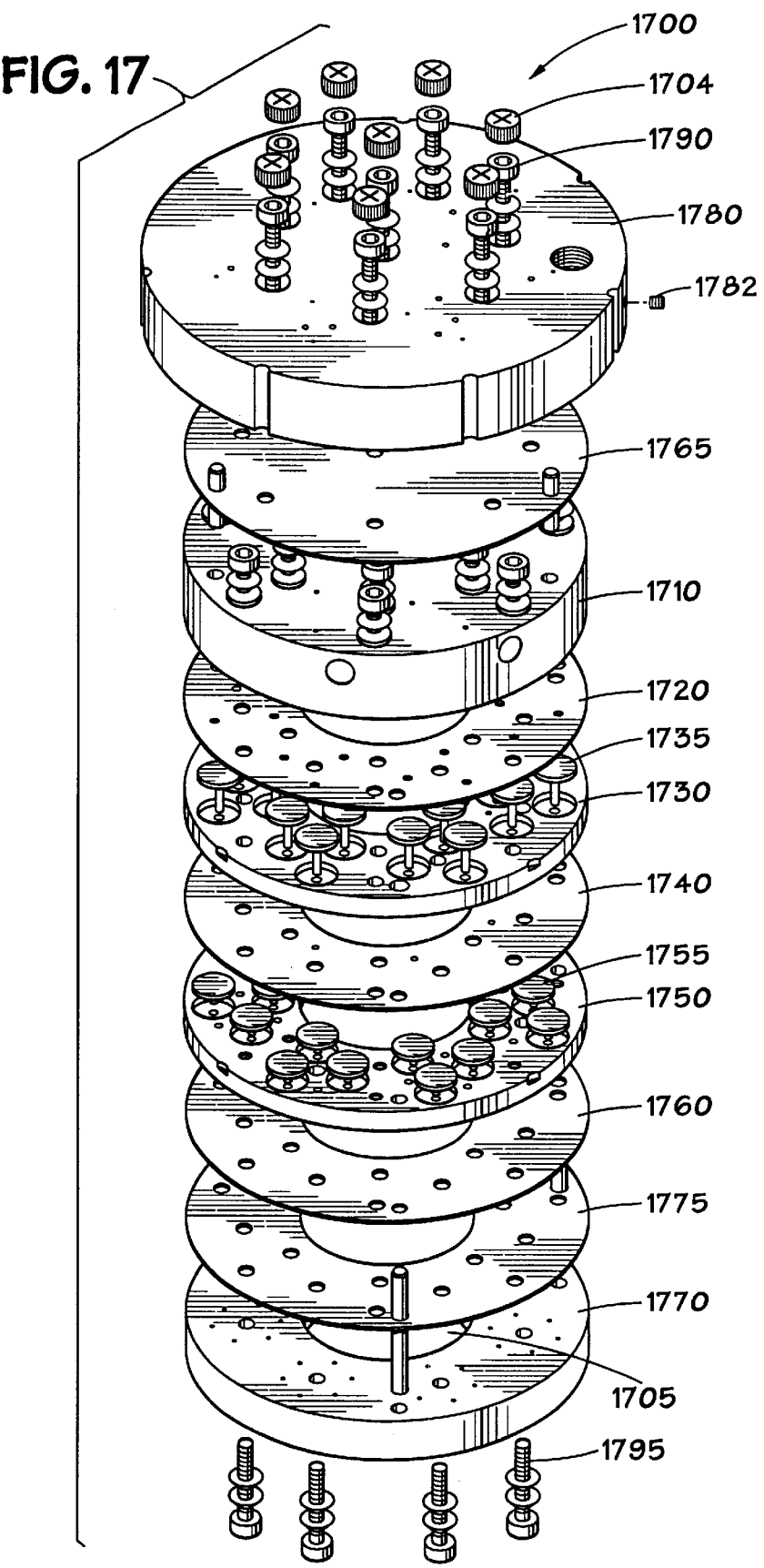
FIG. 17 is an exploded isometric view of a second embodiment of a multi-valve block.

A second embodiment of the invention was developed subsequent to the above embodiment and is shown in FIGS. 17–30. This embodiment of the invention is believed to be improved in a number of respects to the first embodiment. FIG. 17 shows an exploded view of the second embodiment for a multi-valve block 1700 in an inverted configuration. Such an inverted configuration is preferred to simplify assembly. FIG. 17 includes an Ultem™ manifold 1780 with associated Ultem™ plug 1782. Also shown are lower sealing diaphragm 1765, base plate 1710 with carrier gas preheat coil insertion areas, lower actuator diaphragm 1720, lower piston plate 1730 with associated long pistons 1735, upper actuator diaphragms 1740, upper piston plate 1750 with associated short pistons 1755, cushion diaphragm 1760, sealing diaphragm 1775, and primary plate 1770 with associated guide pins 1172. Also shown are an open area 1705 in the center of the multi-valve block, torque screws 1790, and Belleville washers. Insulation plugs 1704 are inserted after torque screws 1790 have been tightened through the manifold 1780. Screws 1795 are also shown.

Figure 18B:
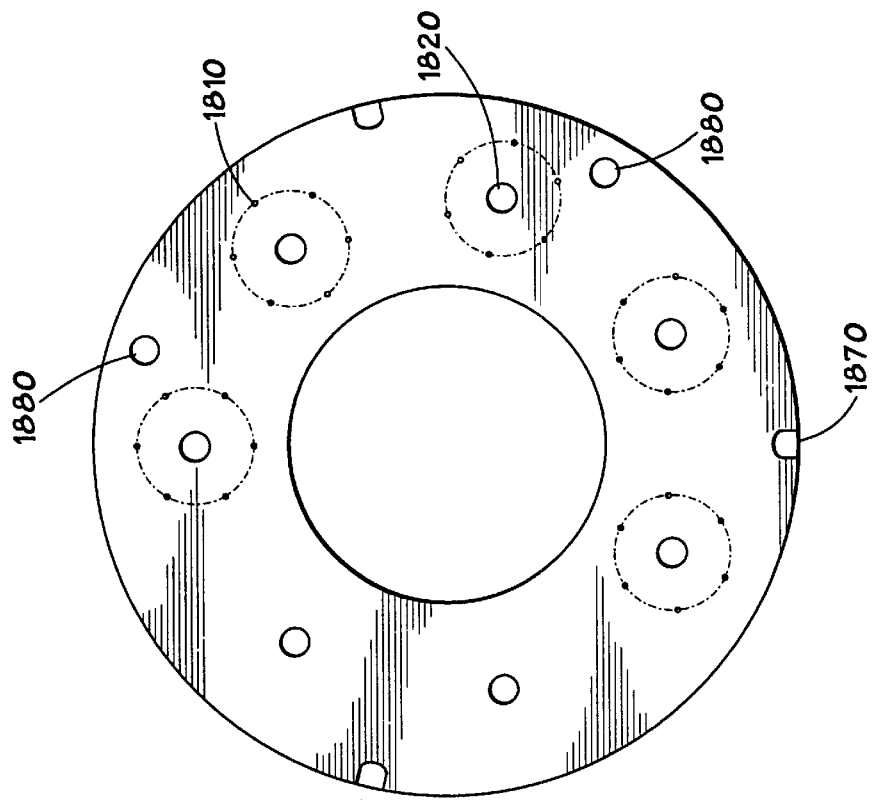
FIG. 18B is a bottom view of a primary plate for the multi-valve block of FIG. 17.
Figure 18A:
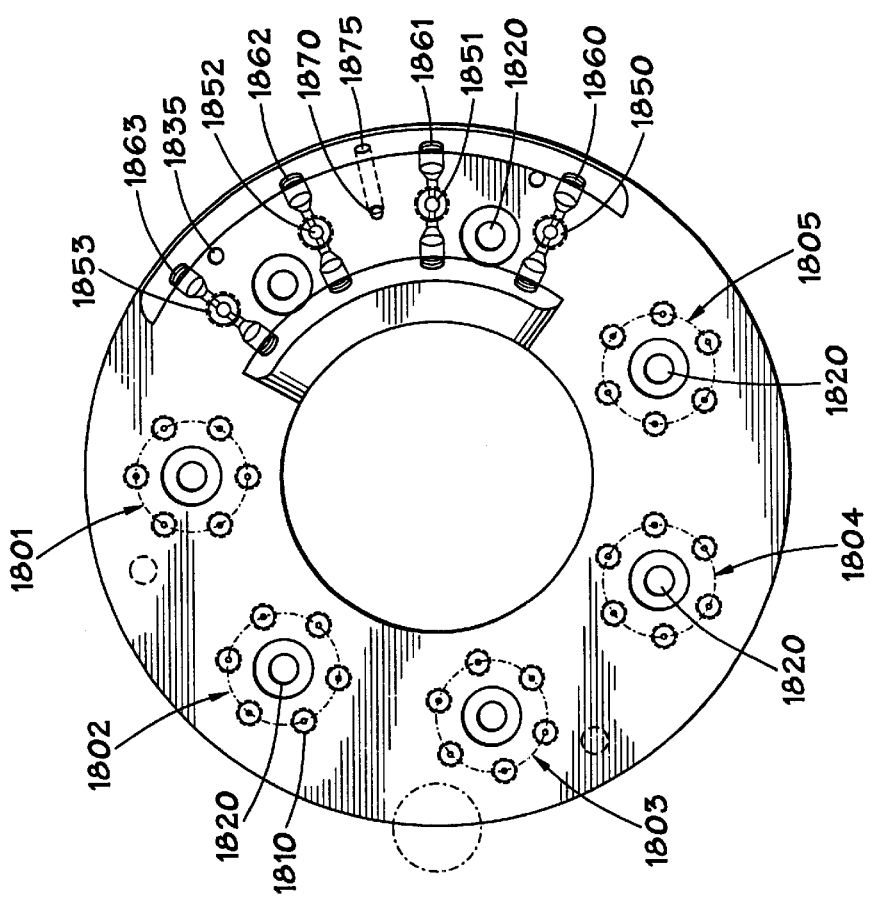
FIG. 18A is a top view of a primary plate for the multi-valve block of FIG. 17.

FIGS. 18A and 18B show the upper and lower view of a primary plate of FIG. 17. Referring now to FIG. 18A, five valves 1801–1805 with 6 ports 1810 each are shown, as well as TCD holes 1850–1853 and associated tubing holes 1860–1863. A hole 1870 is suitable for an RTD heat sensor, and is set by set screws in hole 1875. Holes 1820 are for tightening screws. Hole 1835 is for mounting support of TCD terminal block. In contrast to the hole for the RTD heat sensor of FIG. 10, RTD heat sensor hole 1870 is located in the same radial circle as the TCD holes 1850–1853. As can be appreciated, because the temperature at the TCD is extremely important to the accurate measurement of the gas sample, a temperature sensor (RTD) should be placed as close as possible to the TCD. RTD heat sensor hole 1870 accomplishes this. But further, because of the mass of a multi-valve block, temperature gradients across the block can be significant. The placement of RTD heat sensor hole 1870 in the same radial circle as the TCD holes minimizes error from any temperature gradient across the multi-valve block. FIG. 18B shows a bottom view of the primary plate. Included are holes 1810 corresponding to the valve ports of FIG. 18A, and holes 1820 for tightening screws. Slot 1870 to simplify maintenance and dowel pin holes 1880 are also shown.

Figure 19B:
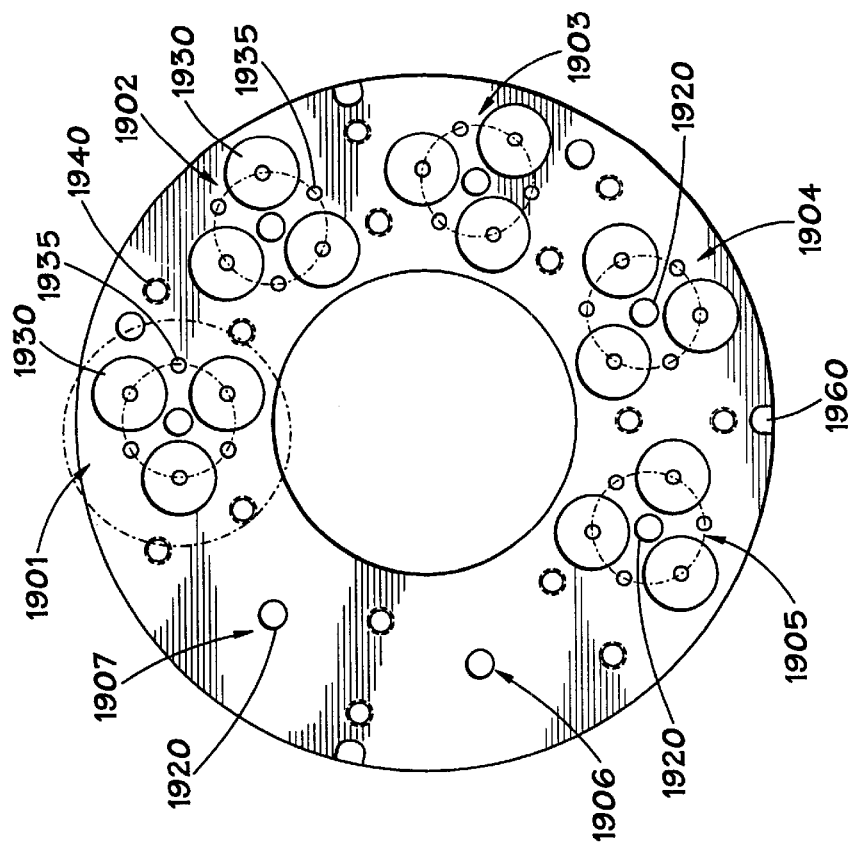
FIG. 19B is a bottom view of an upper piston plate for the multi-valve block of FIG. 17.
Figure 19A:
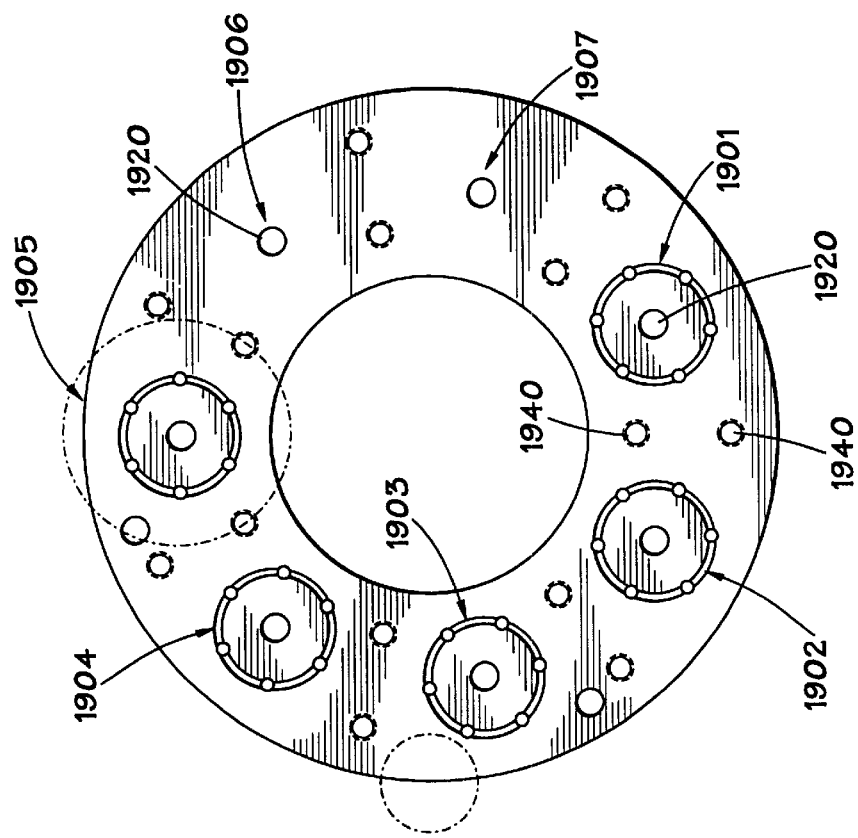
FIG. 19A is a top view of an upper piston plate for the multi-valve block of FIG. 17.

FIGS. 19A and 19B show top and bottom views respectively of the upper piston plate of FIG. 17. Referring to the top view of FIG. 19A, locations 1901–1905 for 5 valves are shown. Screw holes, generally at 1920, are also shown for accepting screws to tighten together the multi-valve block. Holes 1940 are for screws from bottom to tighten together the valve block. As explained with respect to the first embodiment, the dual screw sets of this embodiment considerably simplify maintenance of this embodiment as compared to prior art valves. Turning to the bottom view of the upper piston plate as shown in FIG. 19B, slots 1960 simplify maintenance as generally explained above with respect to the first embodiment. Locations 1901–1905 are for the five valves. Each valve location 1901–1905 includes sufficient room 1930, 1935 for 3 piston bases and 3 piston poles.

Unlike the upper piston plate of the first embodiment as shown in FIG. 7, the second embodiment does not include raised edges to reduce the chance of leakage. The raised edges 740 of the first embodiment were not desirable because significant manufacturing costs were required to obtain such an edge. Instead, some other way of reducing the chance of leakage was sought. The second embodiment reduces the chance of leakage without raised edges by placement of the tightening holes 1920 within the confines of each valve. In particular, the tightening holes 1920 are located at the center of each valve. This results in a leak-free fit for the multi-valve block without the added expense of raised edges.

Figure 20B:
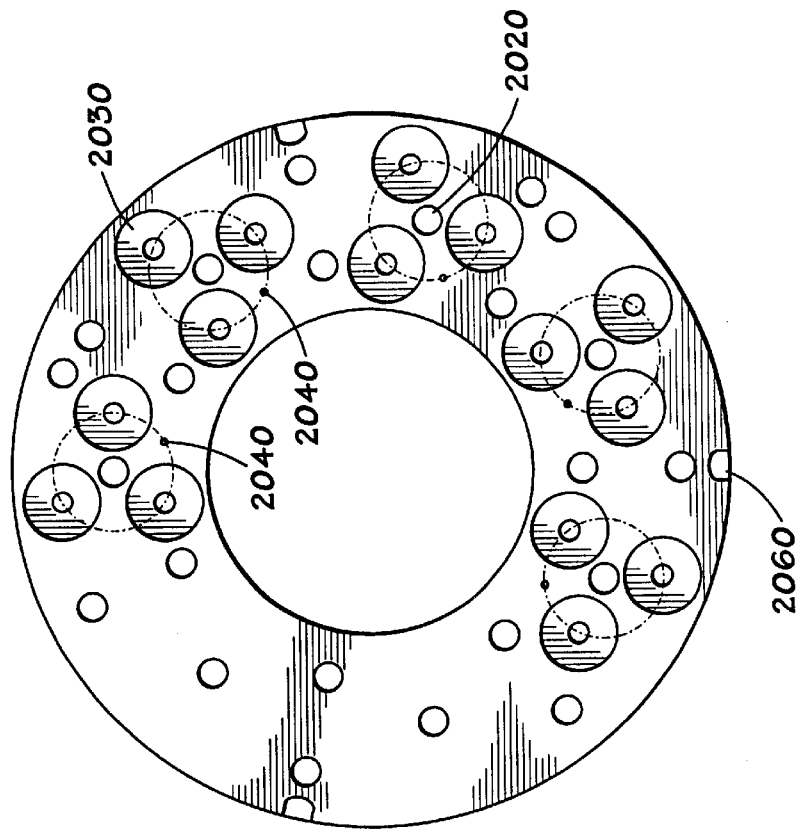
FIG. 20B is a bottom view of a lower piston plate for the multi-valve block of FIG. 17.
Figure 20A:
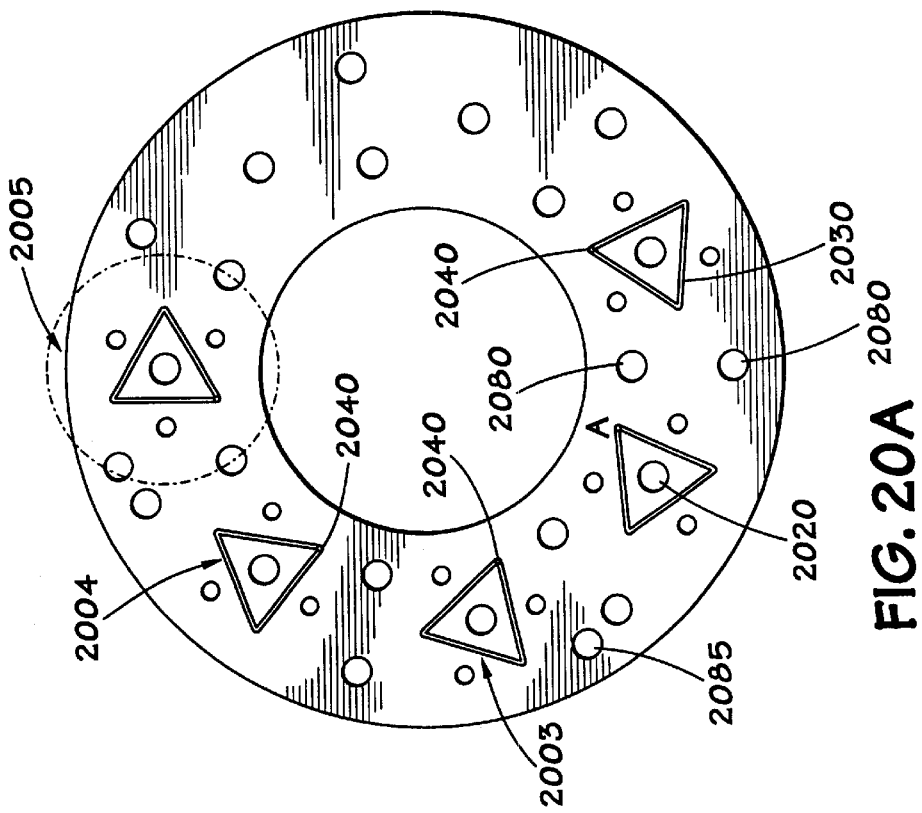
FIG. 20A is a top view of a lower piston plate for the multi-valve block of FIG. 17.

FIGS. 20A and 20B show the lower piston plate of FIG. 17. FIGS. 20A and 20B are the upper and lower views respectively of the lower piston plate. Referring to FIG. 20A, once again, locations 2001–2005 are provided for the five valves. Holes 2080 are screw holes, while holes 2085 are dowel pin holes. Also shown are five triangular grooves 2030 and accompanying holes 2040, as well as holes 2020, to accept tightening screws in the center of each groove 2030. Gas from the actuation ports flows through the holes 2040. The grooves 2030 provide a path for the actuation gas, resulting in a simultaneous elevation and actuation of the short pistons. Because the valves of the illustrated embodiment have six ports, and thus three short pistons per valve, a triangular shape is convenient (but not necessary) to actuate all three short pistons simultaneously. The triangular grooves of the second embodiment are somewhat larger than those of the first as shown in FIG. 8, to accommodate the tightening holes 2020 in their centers. Turning now to the bottom view of FIG. 20B, locations for the valves are shown, in addition to slots 2060. As can be seen, FIG. 20B also includes space 2030 for the base of long pistons 635, tightening screw holes 2020, and other features explained in reference to other Figures herein.

Figure 21B:
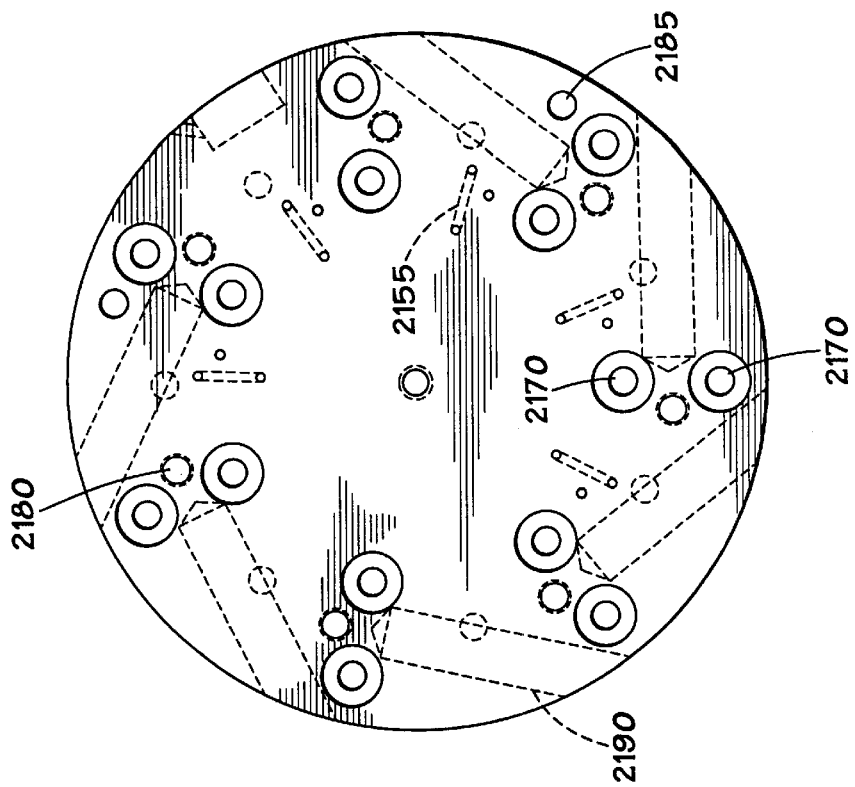
FIG. 21B is a bottom view of a base plate for the multi-valve block of FIG. 17.
Figure 21A:
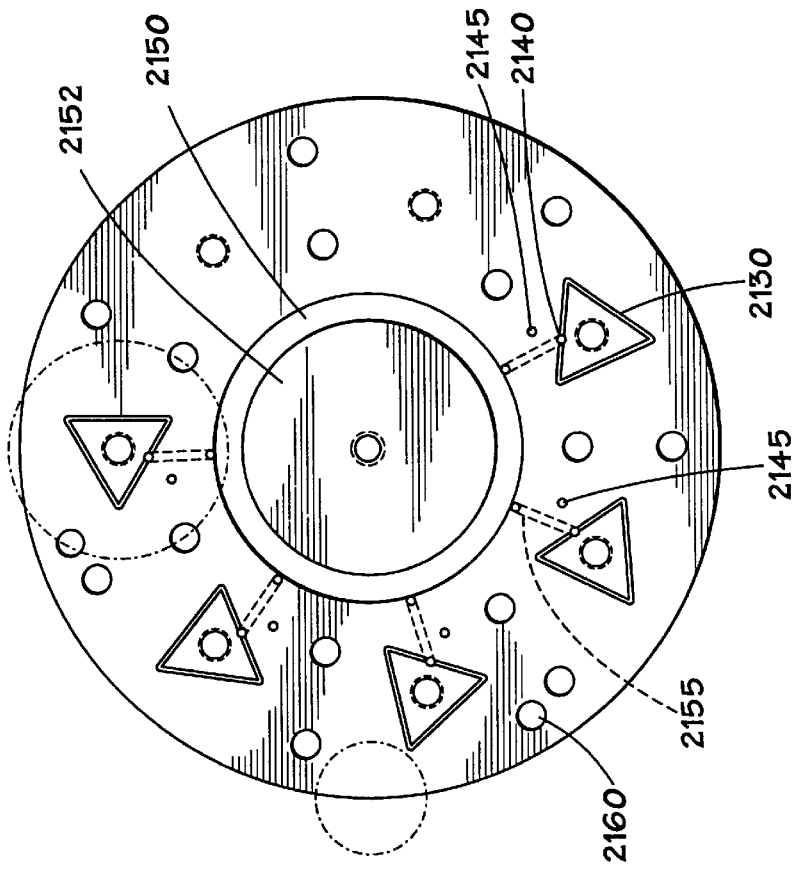
FIG. 21A is a top view of a base plate for the multi-valve block of FIG. 17.

FIGS. 21A and 21B show the top and bottom views respectively of the base plate 1710. Referring to FIG. 21A, holes 2160 and a plurality of triangular grooves 2130 are shown, with each groove encompassing a hole 2140 for actuator gas. Additional holes 2145 forming a path for actuator gas to elevate the short pistons is also shown. Line 2150 indicates an elevation edge down to an area 2152. Area 2152 is an insulating air gap whose function is explained below. Other features are also shown that have been explained in reference to the other Figures. FIG. 21B illustrates the bottom view of the base plate 1710. Shown are actuator gas paths 2155, as well as screw holes 2170 and 2180. Pin holes 2185, and shape silhouettes 2190 are also shown. Shape silhouettes 2190 indicate the locations for the preheat coil insertion areas. The carrier gas in these preheat coils is thus warmed by the multi-valve block. Holes 2170 and 2180 are screw holes. Holes 2185 are dowel pin holes.

Figure 22:
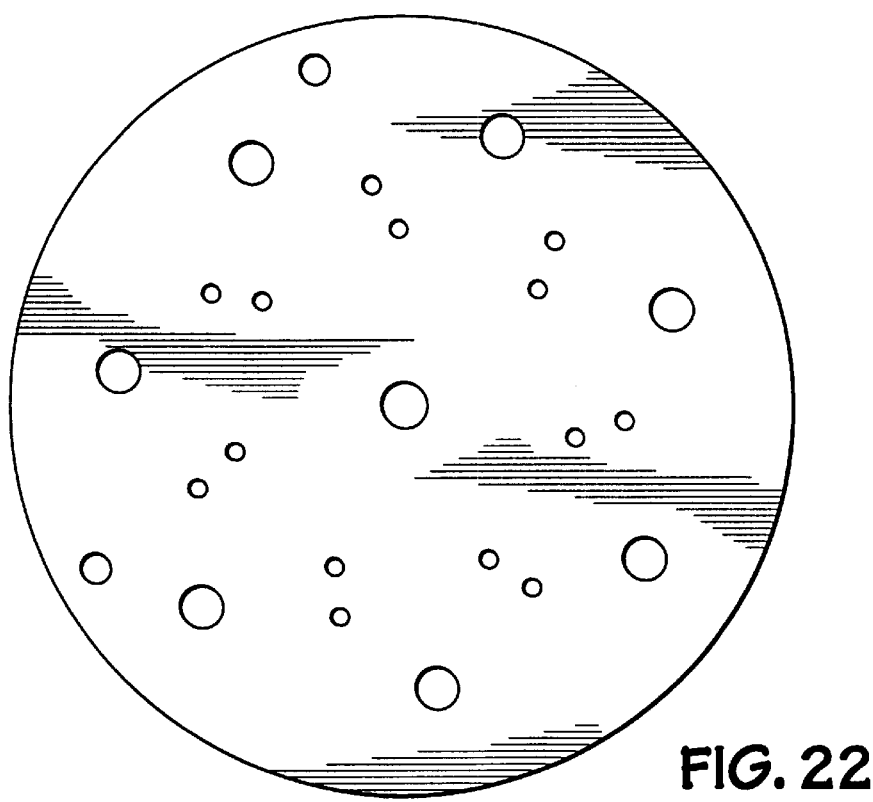
FIG. 22 is a view of a lower sealing diaphragm of FIG. 17.
Figure 24:
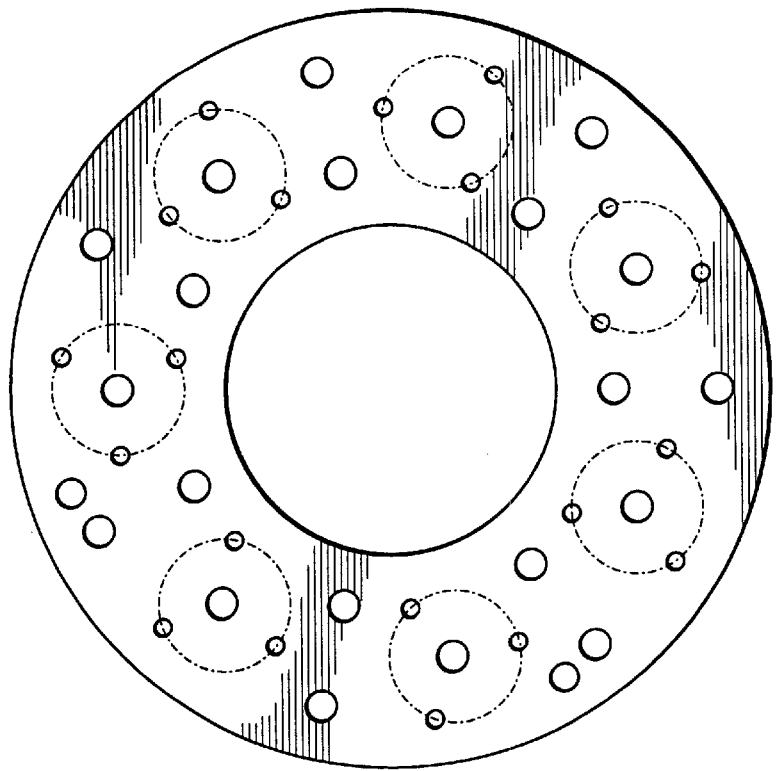
FIG. 24 is a view of a upper actuator diaphragm of FIG. 17.
Figure 23:
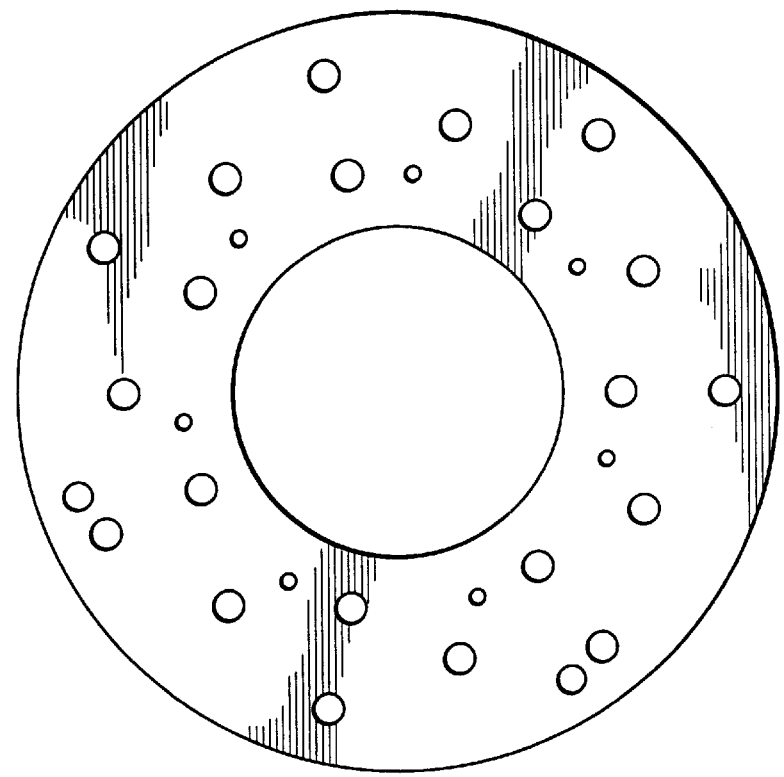
FIG. 23 is a view of a lower actuator diaphragm of FIG. 17.
Figure 26:
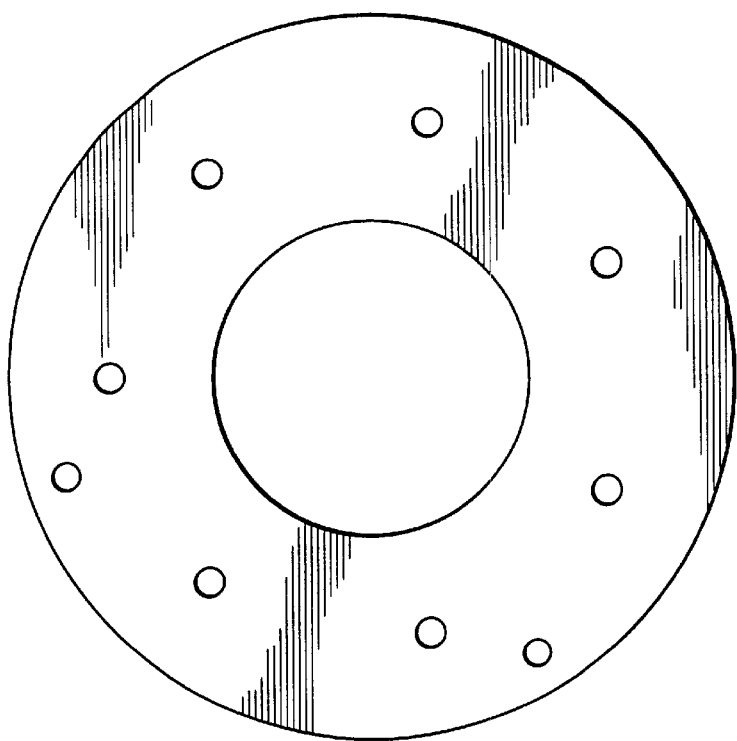
FIG. 26 is a view of an upper sealing diaphragm of FIG. 17.
Figure 25:
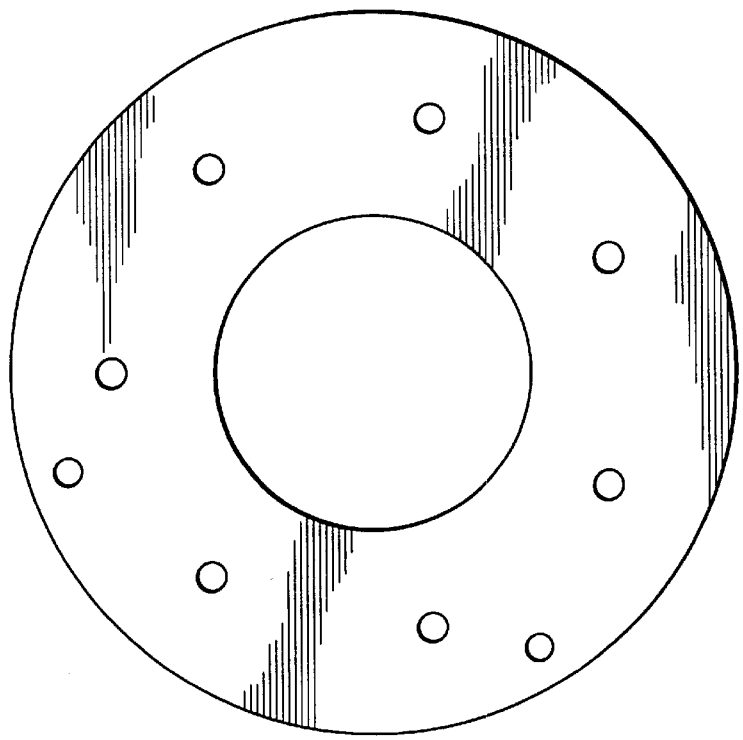
FIG. 25 is a view of a cushion diaphragm of FIG. 17.

FIGS. 22–26 illustrate the diaphragms of the second embodiment. In particular, FIG. 22 illustrates a lower sealing diaphragm of the second embodiment. This diaphragm is preferably a 5 mil Teflon sheet and ensures a leak-free fit between the manifold and the base plate. There is no corresponding diaphragm on the first embodiment. FIG. 23 illustrates a lower actuator diaphragm of the second embodiment. FIG. 24 illustrates an upper actuator diaphragm of the second embodiment. FIG. 25 illustrates a cushion diaphragm of the second embodiment. FIG. 26 illustrates an upper sealing diaphragm of the second embodiment. Each diaphragm includes holes whose purpose is explained with respect to other Figures. These diaphragms are preferably made from the same material as the corresponding diaphragms of the first embodiment.

Figure 27:
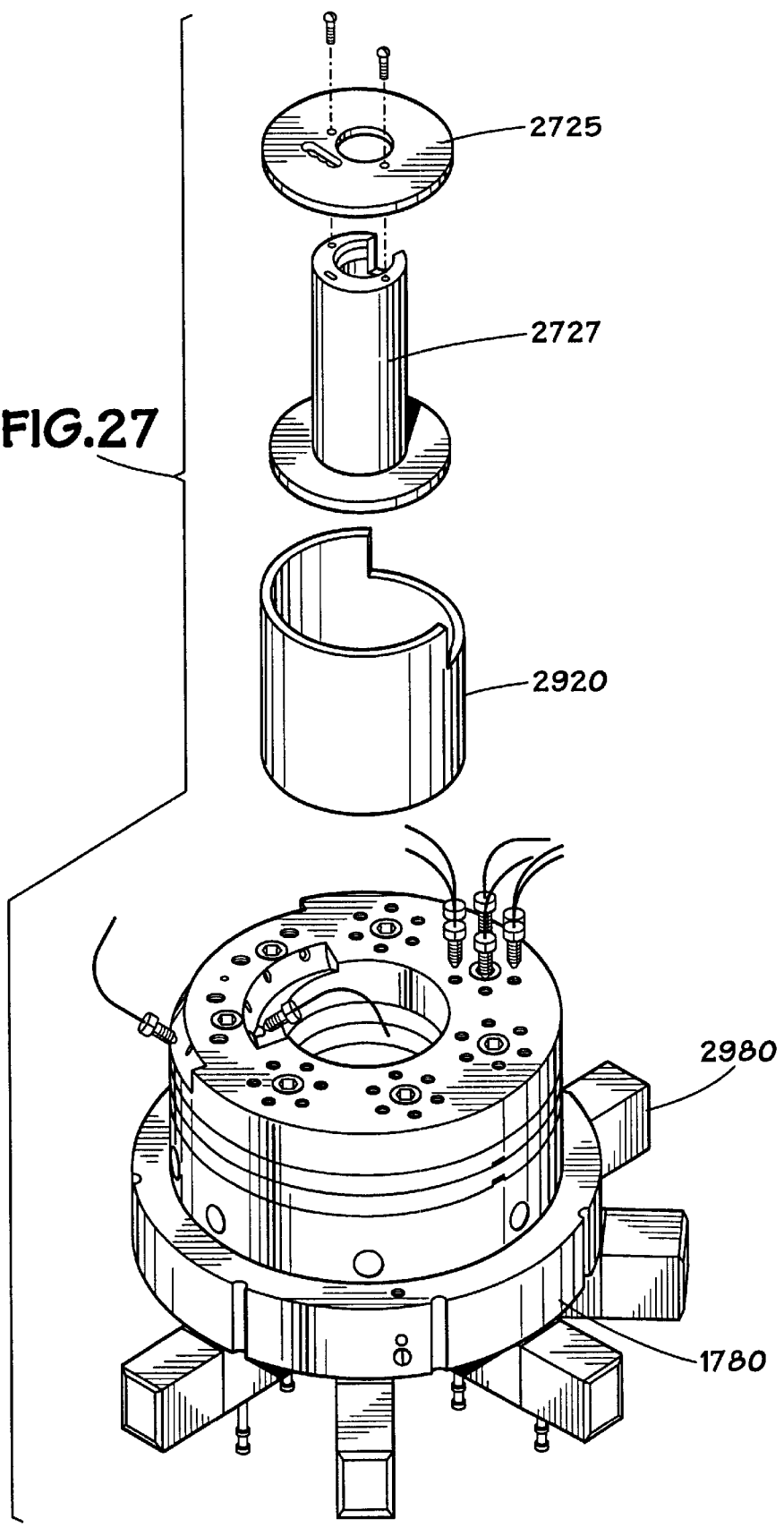
FIG. 27 is a perspective view of a multi-valve assembly including manifold and solenoids.

Referring now to FIG. 27, the second embodiment includes an insulation manifold 1780 instead of the base insulation piece of the first embodiment. Also shown are solenoids 2980, the multi-valve block, a column cup 2920, column support 2727, and a column cover 2745. To simplify viewing of the multi-valve assembly, not shown in FIG. 27 is the remainder of the oven insulation that surrounds the multi-valve assembly. As can be seen, one advantage of manifold 1780 is that the solenoids attach directly to its lower surface and thus tubing between the solenoids and the multi-valve block is eliminated. This elimination of tubing between the solenoids and the multi-valve block results not only in a substantial savings, but also a quicker response time during analysis.

Figure 28B:
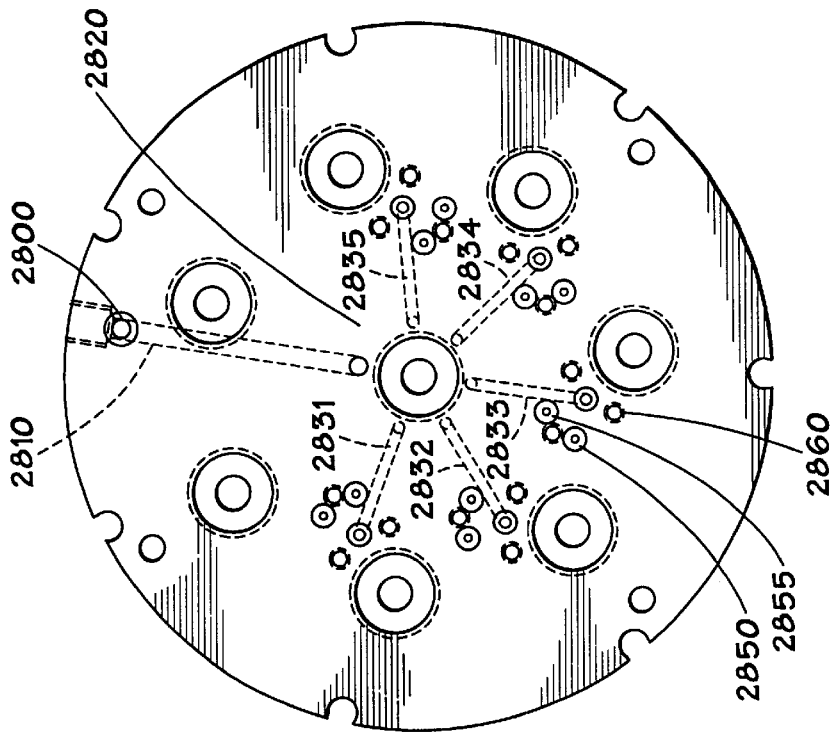
FIG. 28B is a bottom view of a manifold for the multi-valve block of FIG. 17.
Figure 28A:
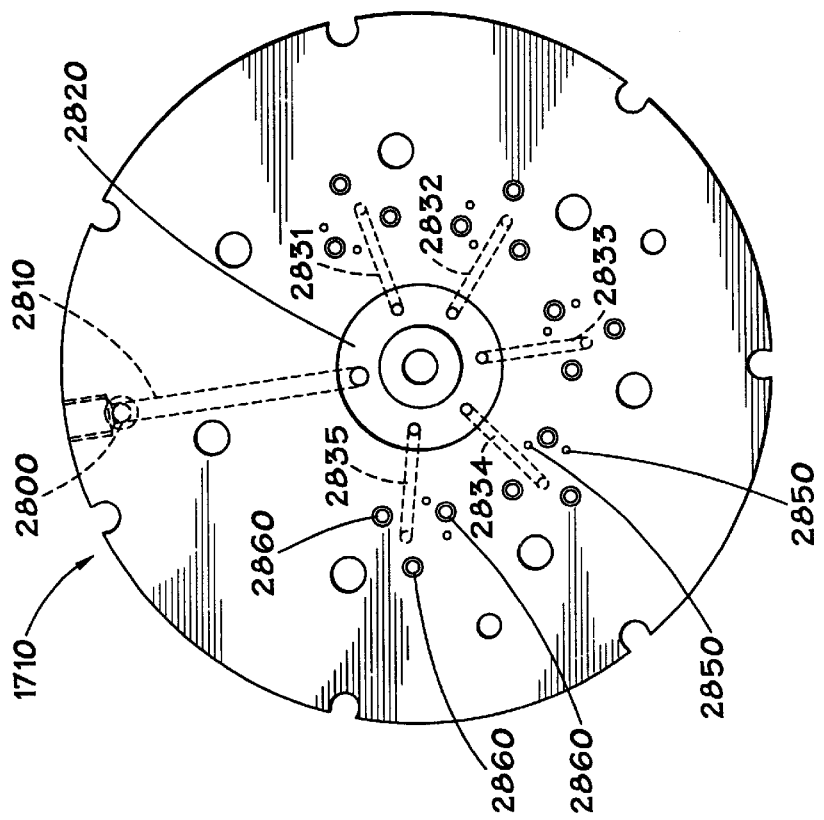
FIG. 28A is a top view of a manifold for the multi-valve block of FIG. 17.

FIGS. 28A and 28B are top and bottom views of the manifold 1780. FIG. 28A shows a universal common line hole 2800 and a common line gas passage 2810 from the common line hole 2800 to a center groove 2820. Also extending from center groove 2820 are a plurality of solenoid actuation passages 2831–2835, one for each solenoid (not shown).

FIG. 28B illustrates many of the same elements as FIG. 28A. Referring now to FIGS. 28A and 28B, during operation, a single tube carrying actuator gas connects to universal common line hole 2800. From there, actuator gas travels through common line gas passage 2810 to center groove 2820. Actuator gas then travels to each individual solenoid via the solenoid passages 2831–2835. At that time, the actuator gas enters each solenoid (not shown), the solenoids being attached firmly to the bottom of the manifold by use of screw holes 2860. The actuator gas travels through the solenoids and exits through the actuator gas holes 2850 or 2855 to place the valves in either an ON or OFF configuration.

Figure 29:
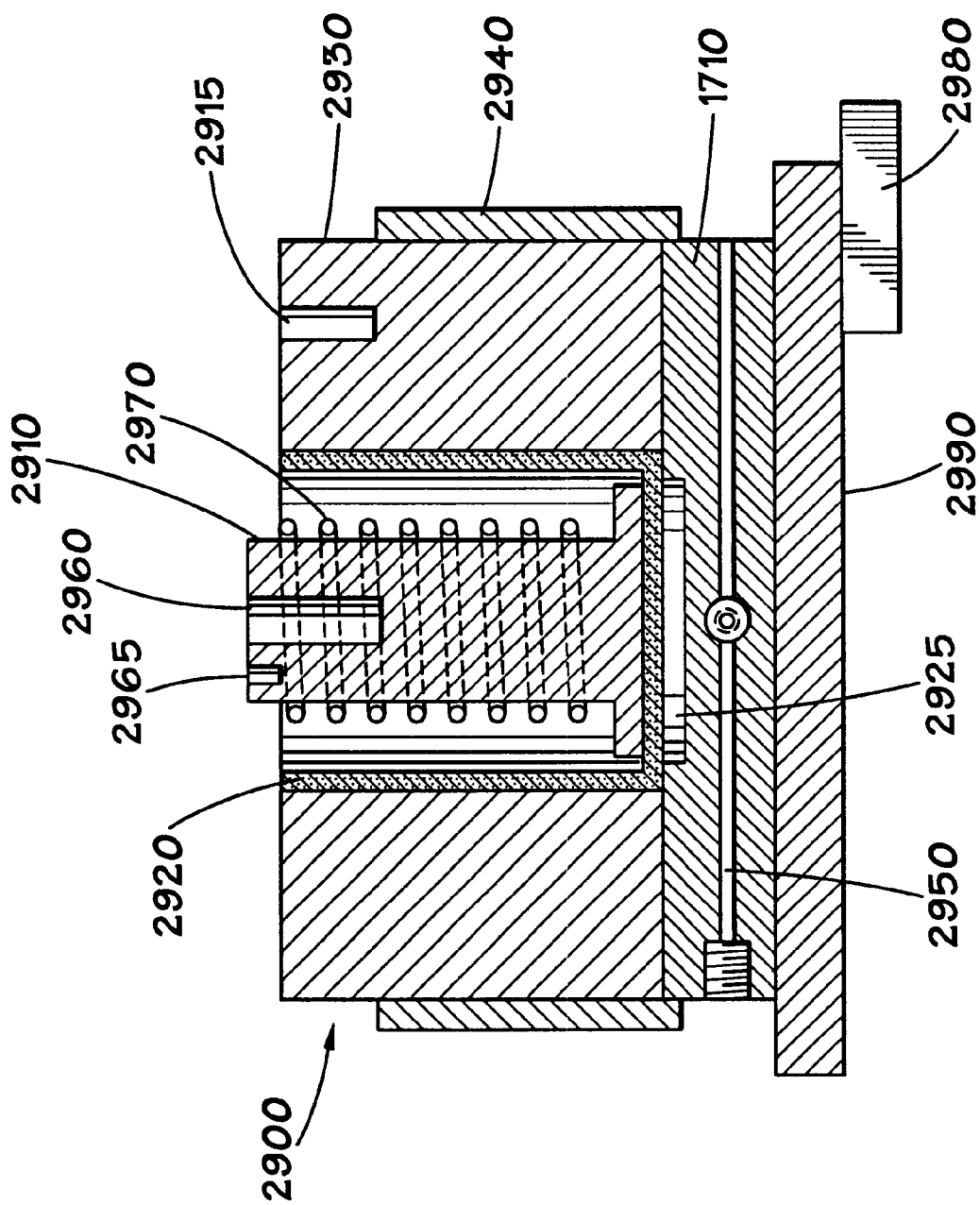
FIG. 29 is a first cross-sectional view of the second embodiment of the multi-valve assembly

FIG. 29 shows the multi-valve assembly of the second embodiment during operation. To simplify viewing, the oven for the multi-valve assembly is not shown. Multi-valve block 2900 includes areas for a first RTD in the same radial plane as the hole for the two TCD pairs 2925, an exterior surface 2930 to the multi-valve block 2900, a band heater 2940 outside of the exterior surface 2930, carrier gas preheat coil 2950, and a base plate 1710. Spool 2910 contains a cartridge heater 2960 and a second RTD 2965. Unlike the first embodiment, a thermal insulation cup 2920 and an air gap 2925 separate the spool and the base plate. The columns 2970 wrap around the spool 2910. An ULTEM manifold 2990 is attached. Also shown are solenoids 2980 connected to the manifold 2990 at its lower end.

Referring back to FIG. 17, a hole or open area 1705 is present in the middle of the multi-valve block. This open area accommodates spool 2910. Thermal insulation cup 2920 and air gap 2925 insulate the spool from the base plate. Thermal insulation cup 2920 is preferably made from nylon. The thermal insulation cup and air gap are significant features of the second embodiment because, as explained, the multi-valve assembly defines two heating zones, each of which should be carefully monitored and maintained. The design of the second embodiment separates these two heating zones by the thermal insulation cup and air gap and therefore helps to achieve temperature stability in each.

Carrier gas preheat tubing 2950 is coiled in holes formed in the body of multi-valve block 2900, and the carrier gas is thus warmed by the heat in the multi-valve block. Band heater 2940 is a DC band heater of approximately 30 Watts power. The substitution of this DC band heater in lieu of the AC band heater of the first embodiment improves the performance of the multi-valve assembly by smoothing out the temperature fluctuations and eliminating electrical noise, and is another improvement over the first embodiment.

Figure 30:
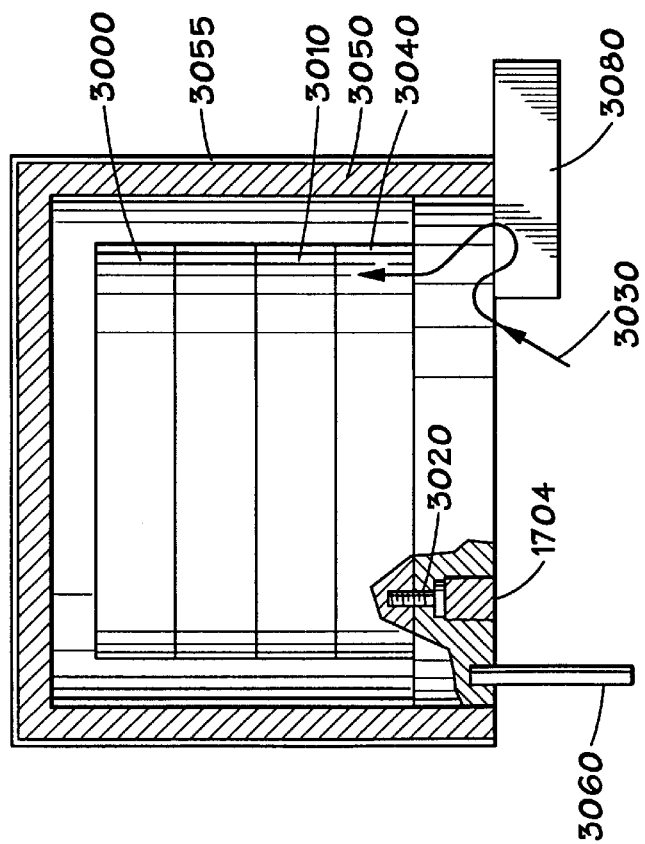
FIG. 30 is a second cross-sectional view of the second embodiment of the multi-valve assembly.

FIG. 30 illustrates a multi-valve assembly including oven insulation. The multi-valve assembly includes a multi-valve block 3000 including a base plate 3010 and manifold 3040. Also shown are torque screws 3020 with associated insulation plugs 1704, standoffs 3060, oven insulation 3050 and solenoid 3080. As can be seen, solenoid 3080 is immediately adjacent the manifold 3040. Actuator gas 3030 flows through the manifold to the solenoid, and then back through the manifold to actuate the appropriate pistons. The oven insulation 3050 of the second embodiment is generally of the same material as the first embodiment, but it is covered with stainless steel around its exterior 3055 to provide reinforcement.

In addition eliminating the need for tubing from the solenoids to the multi-valve assembly, manifold 3040 offers a number of advantages over a bottom piece of insulation. The manifold has good insulation properties. It has been found that ULTEM has the requisite mechanical strength and insulation characteristics, and works very well for such an application, although it is likely not the only appropriate material. ULTEM™ is made by Commercial Plastics, Inc. As an additional feature, instead of being far removed from the multi-valve block, the manifold design allows placement of the solenoids adjacent to the manifold and thus proximate to the base plate. This makes the whole assembly more compact and also increases the response time.

The insulation material has also been modified by placing steel around its exterior. This results in an increased resistance to warping as well as increased durability and ruggedness.

Figure 31:
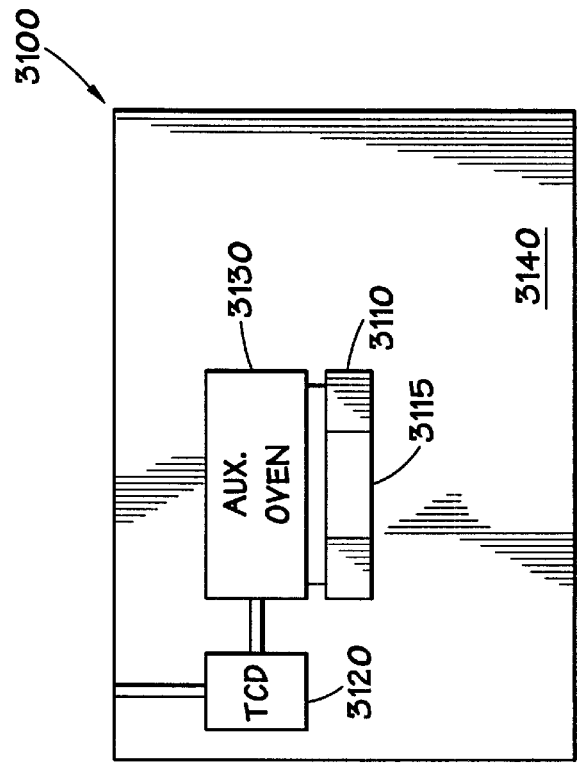
FIG. 31 is an illustration of a gas chromatograph system adapted for use in a refinery environment.

The teachings herein can be adapted to a variety of environments. FIG. 31 shows a multi-valve assembly 3100 suitable for use in a refinery environment. A multi-valve block 3110 including a column area 3115, TCD 3120, auxiliary column oven 3130, and surrounding environment, generally at 3140. With this arrangement, the multi-valve block 3110 has room for a greater number of valves because the TCD 3120 is located outside the multi-valve block. This is a desirable feature when analyzing complex refinery samples. Also shown is an auxiliary oven that may be either warmer or cooler than the multi-valve block. This auxiliary oven provides for a greater number of heating zones for chromatography columns with a corresponding increase in analysis flexibility. Further, because of the refinery environment in which this arrangement can be used, by moving the gas sample analyzer (in this case a TCD outside of the multi-valve block), a more stable temperature is achievable around the TCD 3120. The heater in this embodiment may preferably be an air-bath oven. This further increases the accuracy of the system.

Thus, while preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims that follow, the scope of which shall include all equivalents of the subject matter of the claims.

What is claimed is:

1. A multi-valve assembly comprising:
a plurality of plates and at least one diaphragm attached to form a plurality of valves, each valve capable of being independently activated by actuation pressure,
one of said plurality of plates being a manifold, said manifold including a first common line passage suitable to carry an actuation fluid applying said actuation pressure, and a plurality of actuation passages, there being at least as many of said actuation passages as there are of said valves;
wherein said first common line passage and said plurality of actuation passages are grooves defined by one of said plurality of plates defining said manifold, with said first common line connecting to at least two of said plurality of actuation passages.

2. The multi-valve assembly of claim 1, further comprising:
a plurality of solenoids attached to said manifold.

3. The multi-valve assembly of claim 2, wherein said plurality of solenoids are attached directly to a bottom of said manifold, said bottom being defined with respect to the remainder of said plurality of plates.

4. The multi-valve assembly of claim 1, wherein said common line passage connects to each of said plurality of actuation passages by a groove in said manifold.

5. The multi-valve assembly of claim 4, wherein there is one more actuation passage than there are valves.

6. The multi-valve assembly of claim 4, wherein each of said actuation passages connects to said groove and each of said actuation passages connets as well to a respective tunnel extending through said manifold.

7. The multi-valve assembly of claim 6, further comprising a plurality of solenoids attached to said manifold.

8. The multi-valve assembly of claim 1, wherein said manifold is made from an insulative material.

9. The multi-valve assembly of claim 8, wherein said manifold forms a portion of an insulative oven encapsulating the remainder of said plates.

10. The multi-valve assembly of claim 8, further comprising at least one of said valves attached to a length of tubing holding a fluid,
   said tubing being inserted in insertion holes in at least one of said plates, resulting in an efficient heat transfer between said plate and said tubing.

11. The multi-valve assembly of claim 8, further comprising:
   a set of tightening screws wherein each of said valves defines a valve region and at least one of said tightening screws is inserted through at least one of said valve regions.

12. The multi-valve assembly of claim 1, wherein said plurality of plates is at least three plates.

13. The multi-valve assembly of claim 1, wherein said plurality of plates is at least four plates.

14. The multi-valve assembly of claim 1, wherein each of said valves corresponds to three respective holes extending through said manifold.

15. The multi-valve assembly of claim 1, wherein each of said valves is comprised of a plurality of valve ports.

16. The multi-valve assembly of claim 1, further comprising a plurality of tightening screws, each of said tightening screws corresponding to a single valve, with each tightening screw being inserted within an area defined by its corresponding valve.

17. The multi-valve assembly of claim 16, wherein said valves are each comprised of a plurality of valve ports arranged in a symmetrical manner.

18. The multi-valve assembly of claim 17 wherein each of said tightening screws is inserted through the approximate center of its corresponding valve area.

19. The multi-valve assembly of claim 1, further comprising:
   a plurality of pistons.

20. The multi-valve assembly of claim 1, further comprising:
   a plurality of tightening screws, wherein
      each of said valves is comprised of a plurality of valve ports, said valve ports for each of said valves being arranged in a symmetric manner and thereby defining a valve perimeter for each valve,
      one of said plurality of tightening screws being inserted within each valve perimeter of each valve.

21. The multi-valve assembly of claim 1, wherein said first common line passage is the only common line passage for carrying actuation gas from external said multi-valve assembly to said actuation passages.

22. The multi-valve assembly of claim 1, wherein said first common line connects to all of the actuation passages in said multi-valve assembly.

23. A manifold, comprising:
   a manifold body having an outer surface, a first side, and a second side;
   an actuation gas inlet port formed in said outer surface;
   a first actuation passage connected to said actuation gas inlet port;
   a first actuation gas exit port connected to said first actuation passage, said first actuation gas exit port providing actuation gas to said first side of said manifold;
   first and second actuation gas channels formed through said manifold body to carry actuation gas from said first side of said manifold body to said second side of said manifold body, wherein said first actuation passage and said first and second actuation gas channels are grooves defined in said manifold body.

24. The manifold of claim 23, further comprising:
   a second actuation passage connected to said actuator gas inlet port;
   a second actuation gas exit port connected to said second actuation passage, said second actuation gas exit port providing actuation gas to said first side of said manifold;
   third and fourth actuation gas channels formed through said manifold body to carry actuation gas from said first side of said manifold body to said second side of said manifold body.

25. The manifold of claim 23, wherein said first actuation passage is wholly within said manifold body.

26. The manifold of claim 23, wherein all passages formed in said manifold body connect to said actuation gas inlet port.

* * * * *